United States Patent
Villaverde Corrales et al.

(10) Patent No.: US 11,590,198 B2
(45) Date of Patent: *Feb. 28, 2023

(54) METHODS AND REAGENTS FOR EFFICIENT AND TARGETED DELIVERY OF THERAPEUTIC MOLECULES TO CXCR4 CELLS

(71) Applicants: UNIVERSITAT AUTONOMA DE BARCELONA, Barcelona (ES); INSTITUT RECERCA HOSPITAL DE LA SANTA CREU I SANT PAU, Barcelona (ES); CENTRO DE INVESTIGACION BIOMEDICA EN RED EN BIOINGENIERIA BIOMATERIALES Y NANOMEDICINA (CIBER BBN), Saragossa (ES)

(72) Inventors: Antonio Pedro Villaverde Corrales, Barcelona (ES); Esther Vazquez Gomez, Barcelona (ES); Maria Virtudes Cespedes Navarro, Saragossa (ES); Isolda Casanova Rigat, Saragossa (ES); Neus Ferrer Miralles, Barcelona (ES); Ramon Mangues Bafalluy, Barcelona (ES); Ugutz Unzueta Elorza, Barcelona (ES)

(73) Assignees: UNIVERSITAT AUTONOMA DE BARCELONA, Barcelona (ES); INSTITUT RECERCA HOSPITAL DE LA SANTA CREU I SANT PAU, Barcelona (ES); CENTRO DE INVESTIGACION BIOMEDICA EN RED EN BIOINGENIERIA BIOMATERIALES Y NANOMEDICINA (CIBER BBN), Saragossa (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/026,543

(22) Filed: Sep. 21, 2020

(65) Prior Publication Data
US 2021/0008154 A1 Jan. 14, 2021

Related U.S. Application Data

(63) Continuation of application No. 16/287,583, filed on Feb. 27, 2019, now Pat. No. 10,813,975, which is a continuation of application No. 15/402,795, filed on Jan. 10, 2017, now Pat. No. 10,265,371, which is a continuation of application No. 13/979,560, filed as application No. PCT/EP2012/050513 on Jan. 13, 2012, now Pat. No. 9,580,468.

(30) Foreign Application Priority Data

Jan. 13, 2011 (EP) .................... 11382005

(51) Int. Cl.
| | | |
|---|---|---|
| A61K 38/10 | (2006.01) |
| A61K 47/62 | (2017.01) |
| A61K 47/66 | (2017.01) |
| A61K 47/00 | (2006.01) |
| C07K 7/08 | (2006.01) |
| C07K 14/00 | (2006.01) |
| C12N 15/62 | (2006.01) |
| A61P 31/14 | (2006.01) |
| A61P 35/00 | (2006.01) |
| C07K 14/435 | (2006.01) |

(52) U.S. Cl.
CPC .............. *A61K 38/10* (2013.01); *A61K 47/62* (2017.08); *A61K 47/66* (2017.08); *C07K 7/08* (2013.01); *C07K 14/00* (2013.01); *C07K 14/43504* (2013.01); *C12N 15/62* (2013.01)

(58) Field of Classification Search
CPC ........ A61K 38/10; A61K 47/62; A61K 47/66; A61K 47/00; A61K 47/48; C07K 14/00; C07K 7/08; C07K 14/43504; C12N 15/62; A61P 31/14; A61P 35/00
See application file for complete search history.

(56) References Cited

U.S. PATENT DOCUMENTS

| | | | |
|---|---|---|---|
| 8,394,758 | B2 | 3/2013 | Wu et al. |
| 2002/0102265 | A1 | 8/2002 | Hong et al. |
| 2004/0132642 | A1 | 7/2004 | Hwang |
| 2009/0099060 | A1 | 4/2009 | Bondarev |
| 2012/0064142 | A1 | 3/2012 | Pillay |

FOREIGN PATENT DOCUMENTS

| | | |
|---|---|---|
| EP | 0513613 B1 | 11/1994 |
| WO | WO2006029078 | 3/2006 |
| WO | WO2009046834 | 4/2009 |

OTHER PUBLICATIONS

Yampolsky et al., "The Exchangeability of Amino Acids in Proteins," Genetics, 2005, 170: 1459-1472. (Year: 2005).*
Avino et al., "Efficient bioactive oligonucleotide-protein conjugation for cell-targeted cancer therapy," ChemistryOpen, 2019, 8(3): 382-387. (Year: 2019).*
Tamamura H. et al., "Syntheis and evaluation of bifunctional anti-HIV agents based on specific CXCR4 antagonists-AZT conjunction.", Bioorganic & Medicinal Chemistry, Aug. 2001, LNKD-PUBMED:11504655, vol. 9, No. 8, Aug. 2001 (Aug. 2001), p. 2179-2187.

(Continued)

*Primary Examiner* — Julie Ha
(74) *Attorney, Agent, or Firm* — Greer, Burns & Crain Ltd.

(57) ABSTRACT

Conjugates comprising a targeting moiety specific for the CXCR4 and based on the polyphemusin-derived peptide and a therapeutic or imaging agent are provided. Therapeutic and diagnostic methods with the conjugates which require specific targeting to CXCR4+cells are provided as well.

11 Claims, 13 Drawing Sheets

Specification includes a Sequence Listing.

(56) References Cited

OTHER PUBLICATIONS

Hanaoka H. et al., "Development of a ln-labeled peptide derivative targeting a chemokine receptor, CXCR4, for imaging tumors" Nuclear Medicine and Biology, Elsevier, NY US, vol. 33, No. 4, May 1, 2006, pp. 489-494.

Unzueta, et al., "Intracelular CXCR4 Cell Targeting with T22-empowered Protein-only Nanoparticles", International Journal of Nanomedicine 2012:7 4533-4544.

Rudinger J. "Characteristics of the Amino Acids as Components of a Peptide Hormone Sequence,"Peptide Hormones, JA Parsons Edition, University Park Press, Jun. 1976, pp. 1-7.

"Designing Custom Peptides," from Sigma Genosys, pp. 1-2, Accessed Dec. 16, 2006.

Schinzel R. "The Phosphate Recognition Site of *Escherichia coli* Maltodextrin Phosphorylase," FEBS, Jul. 1191, 286(1,2): pp. 125-128.

Berendsen HJC, "A Glimpse of the Holy Grail?" Science, 1998, 282: pp. 642-643.

Voet D., Biochemistry, Second Edition, John Wiley & Sons, Inc., 1995, pp. 235-241.

Ngo, J.T., "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Bradley, CM, "Limits of Cooperativity in a Structurally Modular Protein: Response of the Notch Ankyrin Domain to Analogous Alanine Substitutions in Each Repeat," J Mol. Biol., 2002, 324: 378-386.

Driessen et al., "Development of Peptide-targeted Lipoplexes to CXCR4-expressing Rat Glioma Cells and Rat Proliferating Endothelial Cells," 2008, Mol. Therapy, 16: 516-524.

Le Bon et al., "AMD3100 Conjugates as Components of Targeted Nonviral Gene Delivery Systems: Synthesis and in Vitro Transfection Efficiency of CXCR4-Expressing Cells", 2004, Bioconjugate Chem., 15:413-423.

Egorova et al., "Chemokine-derived Peptides as Carriers for Gene Delivery to CXCR4 Expressing Cells," 2009, J. Gene Med., 11: 772-781.

Murakami et al., "Inhibitory Mechanism of the CXCR4 Antagonist T22 Against Human Immunodeficiency Virus Type 1 Infection", 1999, J. of Virology, 73(9): 7849-7896.

Chen et al., "Fusion Protein Linkers: Property, Design and Functionality", Adv. Drug Deliv. Rev., Oct. 15, 2013, pp. 1357-1369, vol. 65 (10).

* cited by examiner

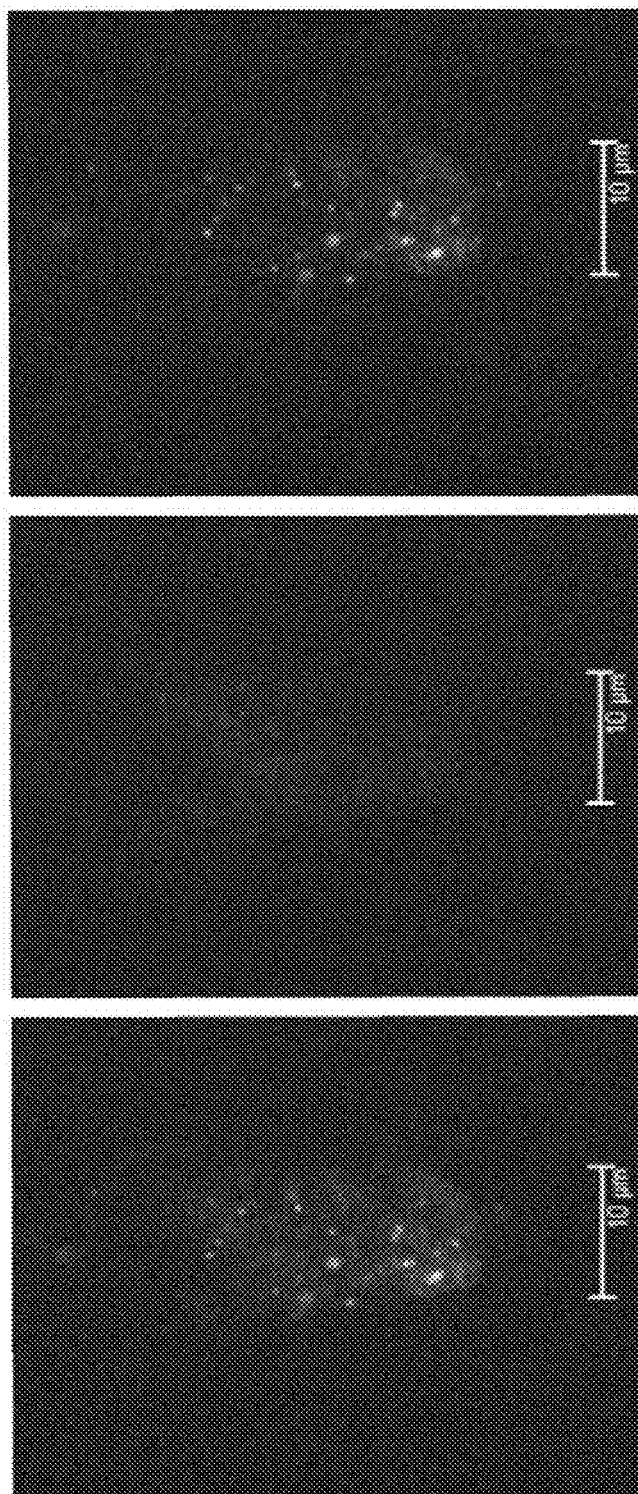

METHODS AND REAGENTS FOR EFFICIENT AND TARGETED DELIVERY OF THERAPEUTIC MOLECULES TO CXCR4 CELLS

CROSS-REFERENCES TO RELATED APPLICATIONS

This application is a continuation application of U.S. patent application Ser. No. 16/287,583, filed Feb. 27, 2019, which is a continuation application of U.S. patent application Ser. No. 15/402,795, filed Jan. 10, 2017, now U.S. Pat. No. 10,265,371, issued Apr. 23, 2019, which is a continuation application of U.S. patent application Ser. No. 13/979,560, filed Nov. 1, 2013, now U.S. Pat. No. 9,580,468, issued Feb. 28, 2017, which is a U.S. national stage of International Application No. PCT/EP2012/050513 with the international filing date of Jan. 13, 2012 which claims the priority benefit of the European Patent Application No. 11382005 filed Jan. 13, 2011, the entire disclosures of which are incorporated herein by reference.

FIELD OF INVENTION

The invention relates to conjugates comprising a targeting moiety and a therapeutic or diagnostic moiety as well as to the uses thereof for therapy.

BACKGROUND OF INVENTION

Chemokine receptors are expressed on the surface of certain cells, which interact with cytokines called chemokines. The CXC chemokine receptor 4 (CXCR4) is a G-protein-coupled receptor that transduces signals of its endogenous ligand, the chemokine CXCL12 (stromal cell-derived factor-1, SDF-I). Following interaction of CXCR4/CXCL12, intracellular calcium ($Ca^{2+}$) ions fluxes are triggered. This causes cellular responses, including chemotaxis, allowing cells to travel within the organism.

CXCR4 is expressed on myeloid cells, T-lymphocytes, B-lymphocytes, epithelial cells, endothelial cells and dendritic cells. Thus, the expression of this molecule on the surface of tumor cells make it a suitable candidate as ligand for the specific targeting of therapeutic compounds to cells expressing said molecule. For instance, WO2006029078 describes fusion constructs comprising a protein translocation domain formed by the Tat protein, the CXCR4-receptor binding DV3 peptide domain and a therapeutic agent which is either a cdk2 antagonist peptide or a p53 activating peptide. These constructs are targeted to cells expressing CXCR4 and, by means of the protein translocation domain, the therapeutic agent is translocated inside the cell. However, these constructs require, in addition to the CXCR4 ligand which acts solely in the docking of the construct to the cell, a translocating domain which delivers the therapeutic agent inside the cell.

Driessen et al. (Molecular Therapy, 2008, 16:516-524) describes the use of a peptide analog, 4-fluorobenzoyl-RR-(L-3-(2-naphthyl)alanine)-CYEK-(1-citrulline)-PYR-(1-citrulline)-CR (SEQ ID NO: 1), covalently linked to a phospholipid to target a lipid-based gene delivery vehicle to CXCR4+-cells. However, this method shows low efficiency and requires increasing expression of CXCR4 on the surface of the target cells by contacting the cells with VEGF prior to the contacting with the conjugates.

Le Bon et al. (Bioconjugate Chem. 2004, 15, 413-423) describe the use of the CXCR4 specific ligands AMD3100 and AMD3100 for promoting specific gene transfer into cells expressing CXCR4 using lipid and polycationic conjugates. However, this method requires the conjugation of a phorbol ester derivative to the polycationic lipid therapeutic agent in order to increase CXCR4 expression on the surface of the target cells.

Egorova et al. (J Gene Med 2009; 11: 772-781) describe conjugates formed by CXCR4 ligands (the peptides KPVSLSYRSPSRFFESH-K9-biotin [(SEQ ID NO: 2)-biotin], KPVSLSYR-K9-biotin [(SEQ ID NO: 3)-biotin] and D-LGASWHRPDK-K9-biotin [(SEQ ID NO: 4)-biotin] and DNA that binds the polylysine region electrostatically and the use thereof for delivery of nucleic acids to CXCR4 positive cells. However, these conjugates have low efficiency and rely on the use of peptides showing agonistic activity towards CXCR4 which may result in an increased tumor proliferation as a response of the stimulation of CXCR4 by the ligands.

Tamamura et al. (Bioinorganic & Medicinal Chemistry, 2001, 9: 2179-2187) describe conjugates of different analoges of the T140 CXCR4 agonist and 3'-azido-3-deoxythymidine (AZT) and their use for preventing HIV-1-induced cytopathogenicity in MT-4 cells. However, no evidence was provided that these conjugates were capable of targeting CXCR4-expressing cells in vivo or that the AZT conjugated to the CXCR4 ligand can be internalized by CXCR4.

Moreover, all these conjugates act by delivering the therapeutic agent to the surface of the cell from where internalization of the said agent requires its binding to specific receptors on the cell surface. Therefore, there is a need in the art for further conjugates suitable for the specific delivery of molecules of interest to CXCR4 cells which overcome the problems of the conjugates described in the prior art and wherein internalization of the therapeutic agent occurs by the use of a CXCR4-targeting molecule which can be internalized by the CXCR4-expressing cells together with the therapeutic agent bound to it.

SUMMARY OF THE INVENTION

In a first aspect, the invention relates to a conjugate comprising
(i) a targeting peptide comprising the sequence RRWCYRKCYKGYCYRKCR (SEQ ID NO: 5) or a functionally equivalent variant thereof and
(ii) a therapeutic agent
wherein the targeting peptide is capable of specifically binding to CXCR4 and promoting internalization of the therapeutic agent in a cell expressing CXCR4. In further aspects, the invention relates to a polynucleotide encoding a conjugate according to the invention, a vector comprising said polynucleotide and a host cell comprising said polynucleotide or said vector.

In a further aspect, the invention relates to a conjugate, a polynucleotide, a vector or a host cell according to the invention for use in medicine.

In a further aspect, the invention relates to a conjugate, a polynucleotide, a vector or a host cell according to the invention for use in a method for the treatment of cancer wherein said cancer contains cells that express CXCR4.

In a further aspect, the invention relates to a conjugate, a polynucleotide, a vector or a host cell according to the invention for use in a method of treatment of a disease associated with HIV infection.

BRIEF DESCRIPTION OF THE FIGURES

FIG. 3A Green fluorescent protein emission determined by flow cytometry of untreated HeLa cells and 20 h after being exposed to different concentrations of T22-GFP-H6. FIGS. 3F-3H are TEM images of randomly T22-GFP-H6 particles in Tris 20 mM +NaCl 500 mM buffer. FIG. 3I 2 µM T22-GFP-H6 internalization by confocal microscopy at 30 min (FIG. 3J), 1 h (FIG. 3K), 2 h (FIG. 3L), 3 h (FIG. 3M), 4 h (FIG. 3N), and 24 h (FIG. 3O).

FIGS. 4A-4D. Evaluation of DNA-binding and gene transfer properties of T22-GFP-H6. FIG. 4A Retardation of plasmid DNA migration in agarose gel electrophoresis promoted by increasing amounts of T22-GFP-H6. FIG. 4B, FIG. 4C and FIG. 4D Confocal microscopy of a HeLa cell with T22-GFP-H6 protein inside (intense signal dots), which expresses td tomato gene (soft signal), 24 h after exposition to T22-GFP-H6-td tomato gene complex.

DETAILED DESCRIPTION OF THE INVENTION

Figure 1A:
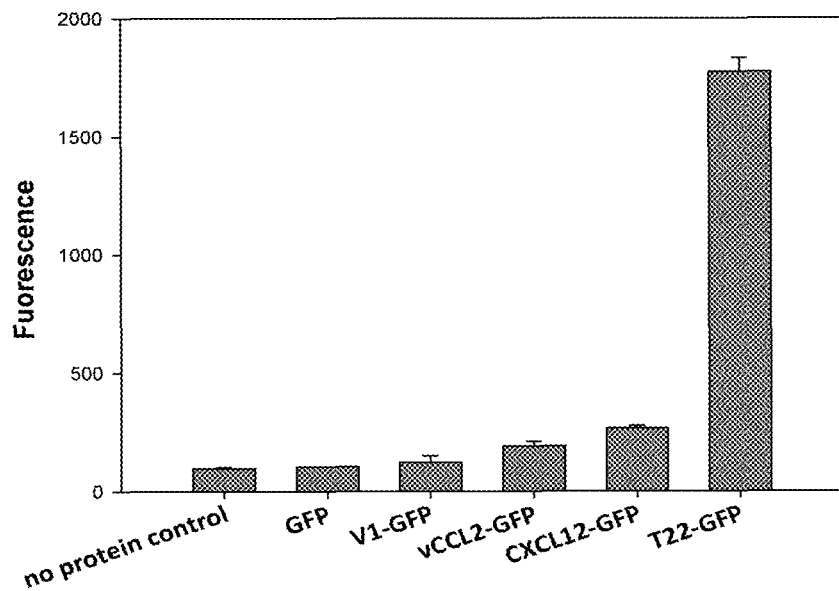
FIGS. 1A-1B. Internalization of T22, vCCL2, V1 and CXCL12-GFP-H6 fusion proteins in HeLa cells. Green fluorescent protein emission determined by flow cytometry, of untreated HeLa cells and 20 h after being exposed to 0.6 µM of the CXCR4 ligand-GFP-H6 fusion proteins T22-GFP-H6, V1-GFP-H6, vCCL2-GFP-H6 and CXCL12-GFP-H6 in FIG. 1A PBS+10% glycerol buffer or FIG. 1B in Tris 20 mM+NaCl 500 mM buffer. HeLa cells had a prolonged trypsin treatment (see experimental section) to eliminate potential residual fluorescent emission due to eventual cell surface attached GFP fusion proteins.
Figure 1B:
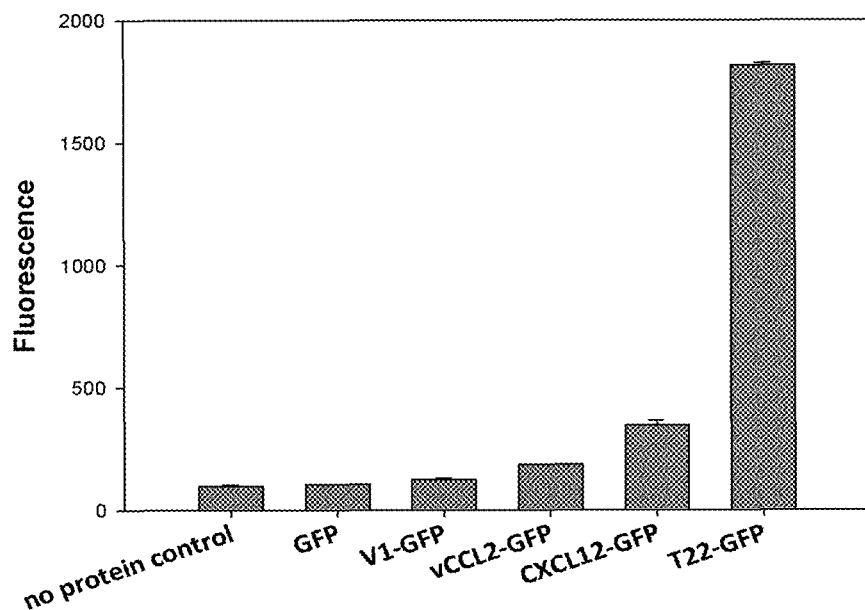
Figure 2A:
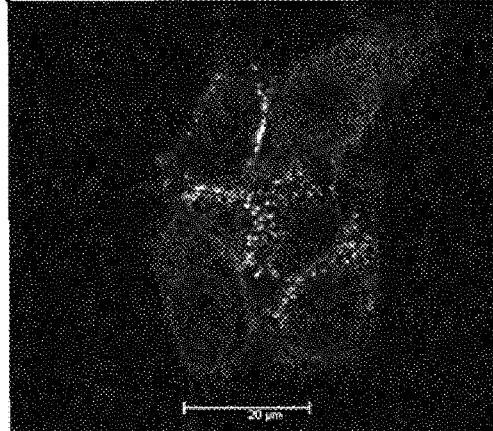
FIGS. 2A, 2B, 2C, 2D. Confocal analysis of T22, vCCL2, V1 and CXCL12-GFP-H6 upon internalization in HeLa cells. The cell membrane was labelled with CellMask and cell DNA was labelled with Hoechst 33342. CXCR4 ligand-GFP-H6 fusion proteins produced a green signal that can be seen as intense dots inside the cells. Cultured cells were exposed for 20 h to 0.6 µM of FIG. 2A T22-GFP-H6, FIG. 2B V1-GFP-H6, FIG. 2C vCCL2-GFP-H6 and FIG. 2D CXCL12-GFP-H6 proteins dissolved in PBS+10% glycerol buffer.
Figure 2B:
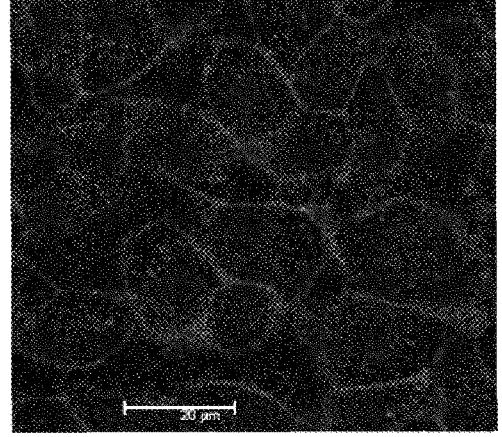
Figure 2C:
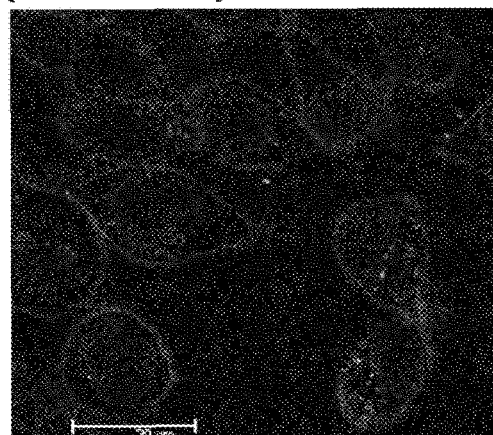
Figure 2D:
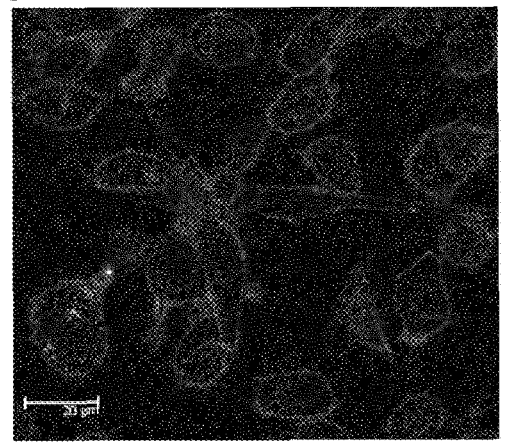

The authors of the present invention have observed that, surprisingly, a peptide derived from the sequence of poliphemusin II ([Tyr$^{5,12}$,Lys$^7$]-polyphemusin II, hereinafter T22 peptide) is able to promote the internalization of functional and soluble fused compounds into target CXCR4+ cells. As shown for instance in the examples of the present invention, a fusion protein comprising the T22 peptide and a marker protein can be internalized and released in the cytoplasm. The result was unexpected since, although this peptide had been reported in the prior art as CXCR4 ligand (see Murakami et al. J. Virol., 1999, 73:7489-7496), no increase in the internalization rates of the receptor was reported as a result of the binding of the peptide to the receptor. The results were also surprising since the molecule that could be internalized when coupled to the T22 peptide was a 26 kDa polypeptide. This type of molecule, due to their relatively large size, is internalized with a much lower efficiency than small organic molecules. Moreover, the experiments provided in the present invention illustrate that other high-affinity CXCR4 ligands (the V1 peptide corresponding to the N-terminal region of vCCL2, the complete vCCL2 or CXCL12/SDF-1), while capable of promoting endocytosis of the ligand, did not lead to endosomal escape of the proteins attached to said peptide.

Therapeutic Conjugates of the Invention

Thus, in a first aspect, the invention relates to a conjugate comprising
(i) a targeting peptide comprising the sequence RRWCYRKCYKGYCYRKCR (SEQ ID NO: 5) or a functionally equivalent variant thereof and
(ii) a therapeutic agent
wherein the targeting peptide is capable of specifically binding to CXCR4 and promoting internalization of the therapeutic agent in a CXCR4 expressing cell.

A. The Targeting Peptide

The first component of the conjugates of the invention is a targeting peptide comprising the sequence RRWCYRKCYKGYCYRKCR (SEQ ID NO: 5) (hereinafter the T22 peptide) or a functionally equivalent variant thereof.

The term "peptide", as used herein, generally refers to a linear chain of around 2 to 40 amino acid residues joined together with peptide bonds.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

The term "functionally equivalent variant", as used herein, refers to any variant of the T22 which contain insertions, deletions or substitutions of one or more amino acids and which conserve substantially the capacity of T22 for interacting with CXCR4 and for promoting internalization and/or endosomal escape of therapeutic molecules attached to it. A suitable assay for determining whether a given peptide can be seen as a functionally equivalent variant thereof is, for instance, the assay described in example 1 of the present invention. In this assay, a putative functionally equivalent variant of T22 variant is fused in frame with a marker polypeptide (e.g. a fluorescent protein) and incubated with a cell expressing CXCR4 (e.g. HeLa cells). If the peptide is a functionally equivalent variant of T22, the marker protein will be internalized and expressed in the cytosol.

In one embodiment, the targeting peptide is the selected from the group consisting of:
  the T140 peptide having the sequence RRX$_1$CYRKX$_2$PYRX$_3$CR (SEQ ID NO: 6) wherein X$_1$ is L-3-(2-naphtyl)alanine, X$_2$ is D-Lys and X$_3$ is L-Citrulline.
  the TN14003 peptide having the sequence RRX$_1$CYX$_2$KX$_3$PYRX$_4$CR (SEQ ID NO: 7) wherein X$_1$ is L-3-(2-naphtyl)alanine, X$_2$ is Cit, X$_3$ is dLys and X$_4$ is L-Citrulline,
  the TC14012 peptide having the sequence RRX$_1$CYEKX$_2$PYRX$_3$CR (SEQ ID NO: 8) wherein X$_1$ is L-3-(2-naphtyl)alanine, X$_2$ is d-Citrulline and X$_3$ is L-Citrulline,
  the TE14011 peptide having the sequence RRX$_1$CYX$_2$KX$_3$PYRX$_4$CR (SEQ ID NO: 9) wherein X$_1$ is L-3-(2-naphtyl)alanine, X$_2$ is L-Citrulline, X$_3$ is dGlu and X$_4$ is L-Citrulline and
  the TZ14011 peptide having the sequence RRX$_1$CYX$_2$KX$_3$PYRX$_4$CR (SEQ ID NO: 9) wherein X$_1$ is L-3-(2-naphtyl)alanine, X$_2$ is L-Citrulline, X$_3$ is D-Lys and X$_4$ is L-Citrulline or the variant thereof wherein the N-terminal Arginine residue is acetylated (known Ac-TZ14011).

In another embodiment, the targeting peptide is not a peptide selected from the group consisting of the T140 peptide, TN14003 peptide, TC14012 peptide, the TE14011, the TZ14011 or the N-terminally acetylated variant of TZ14011 and the T131 peptide having the sequence RRYCYRKX$_1$PYRKCR wherein X$_1$ is D-Lys (SEQ ID NO:37).

The skilled person will appreciate that the tertiary structure of the targeting peptides may depend on the presence of disulfide bridges between the cysteine residues found in the primary structure. In a preferred embodiment, the T22 peptide contains at least one disulfide bridge between cysteines at positions 4 and 17. In another preferred embodiment, the T22 peptide contains at least one disulfide bridge between cysteines at positions 8 and 13. In a still more preferred embodiment, the T22 peptide contains a first disulfide bridge between cysteines at positions 4 and 17 and a second disulfide bridge between cysteines at positions 8 and 13.

The T22 peptide may further comprise a methionine residue at the N-terminal position.

Suitable functional variants of the targeting peptide are those showing a degree of identity with respect to the T22 peptide of about greater than 25% amino acid sequence identity, such as 25% 40%, 60%, 70%, 80%, 90%, 91%, 92%, 93%, 94%, 95%, 96%, 97%, 98% or 99%. The degree of identity between two polypeptides is determined using computer algorithms and methods that are widely known for the persons skilled in the art. The identity between two amino acid sequences is preferably determined by using the BLASTP algorithm as described previously [BLAST Manual, Altschul, S., et al., NCBI NLM NIH Bethesda, Md. 20894, Altschul, S., et al., J. Mol. Biol. 1990; 215: 403-410]. The proteins of the invention may include post-translational modifications, such as glycosylation, acetylation, isoprenylation, myristoylation, proteolytic processing, etc.

Alternatively, suitable functional variants of the targeting peptide are those wherein one or more positions contain an amino acid which is a conservative substitution of the amino acid present in the T22 protein mentioned above. "Conservative amino acid substitutions" result from replacing one amino acid with another having similar structural and/or chemical properties For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). Selection of such conservative amino acid substitutions is within the skill of one of ordinary skill in the art and is described, for example by Dordo et al. et al., (J. Mol. Biol, 1999, 217; 721-739) and Taylor et al., (J. Theor. Biol., 1986, 119:205-218).

The first component is capable of specifically binding to CXCR4 and promoting internalization of the second component.

The term "CXCR4", as used herein, refers to a G protein-coupled, seven-transmembrane chemokine receptor. Like other chemokine receptors, CXCR4 plays an important role in immune and inflammatory responses by mediating the directional migration and activation of leukocytes CXCR4 is expressed or overexpressed in a variety of cancer cell lines and tissues including breast, prostate, lung, ovarian, colon, pancreatic, kidney, and brain, as well as non-Hodgkin's lymphoma and chronic lymphocytic leukemia. The only known ligand to CXCR4 is stromal cell-derived factor-1 (SDF-1, or CXCL12). The interaction between CXCR4 and SDF-1 plays an important role in multiple phases of tumorigenesis, including tumor growth, invasion, angiogenesis, and metastasis.

Binding affinity is measured, for instance, as described by Tamamura et al. by the oil-cushion method (see Hesselgesset et al, 1998, J. Immunol., 160:877-883) comprising contacting the peptide with CXCR4-transfected cell line (e.g. CHO cells) and a labeled CXCR4 ligand (e.g. $^{125}$I-SDF-1α) and measuring the inhibition percentage of the targeting peptide against the binding of the labeled CXCR4 ligand.

The expression "specifically binding to CXCR4", as used herein refers to the ability of the conjugates of the invention to bind more frequently, more rapidly, with greater duration and/or with greater affinity to CXCR4 or cell expressing same than it does with alternative receptors or cells without substantially binding to other molecules.

Binding affinity is measured, for instance, as described by Tamamura et al. by the oil-cushion method (see Hesselgesset et al, 1998, J. Immunol., 160:877-883) comprising contacting the peptide with CXCR4-transfected cell line (e.g. CHO cells) and a labeled CXCR4 ligand (e.g. $^{125}$I-SDF-1α) and measuring the inhibition percentage of the targeting peptide against the binding of the labeled CXCR4 ligand.

Specific binding can be exhibited, e.g., by a low affinity targeting agent having a Kd of at least about $10^{-4}$ M. For example, if CXCR4 has more than one binding site for a ligand, a ligand having low affinity can be useful for targeting. Specific binding also can be exhibited by a high affinity ligands, e.g. a ligand having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity-targeting ligands are useful for incorporation in the conjugates of the present invention.

As used herein, "internalization" refers to a process by which a molecule or a construct comprising a molecule binds to a target element on the outer surface of the cell membrane and the resulting complex is internalized by the cell. Internalization may be followed up by dissociation of the resulting complex within the cytoplasm. The target element, along with the molecule or the construct, may then localize to a specific cellular compartment.

The ability of the conjugate of the invention to be internalized by cells expressing CXCR4 may be conveniently determined by fluorescence methods in the case that the conjugate comprises a fluorescent protein, such as GFP. Such fusion proteins can be obtained by preparing a recombinant nucleic acid wherein the nucleic acids encoding the T22 peptide and the fluorescent protein are fused in frame and expressed in an adequate host cell or organism. The fusion protein is then contacted with a culture of cells expressing CXCR4 or in vivo with a tissue which expresses CXCR4 for an appropriate amount of time, after which fluorescence microscopy may be used to determine whether the construct penetrated the cell. Presence of fluorescence in the cytoplasm may be further investigated by comparing the fluorescence microscopy image resulting from the fluorescent protein to that obtained with a known cytoplasmic stain.

Alternatively, it is also possible to test the ability of the conjugate of the invention to be internalized by cells expressing CXCR4 by preparing non-covalent complexes between a fusion protein comprising the first component of the conjugate and a polynucleotide encoding a fluorescent protein (e.g. the TdTomato gene, encoding a red fluorescent protein). The complex is then contacted with a culture of cells expressing CXCR4 or in vivo with a tissue which expresses CXCR4 for an appropriate amount of time, after which fluorescence microscopy may be used to determine whether the construct penetrated the cell and the gene encoding the fluorescent protein has been expressed. Presence of fluorescence in the nucleus may be further investigated by comparing the fluorescence microscopy image resulting from the fluorescent protein to that obtained with a known nuclear stain (e.g. DAPI).

In a preferred embodiment, the first component is capable of specifically binding to CXCR4 and promoting internalization and endosomal escape of the second component.

The expression "promoting endosomal escape", as used herein, refers to the ability of the targeting peptide to induce the release of the conjugates from the endosomal compartment after internalization by receptor-mediated endocytosis.

B. The Therapeutic Agent

The therapeutic agent (also known herein as second component of the conjugate of the invention) is a compound of therapeutic interest.

The term "therapeutic" is used in a generic sense and includes treating agents, prophylactic agents, and replacement agents.

The nature of the therapeutic agent is not particularly limiting as long as it can be conjugated to the targeting peptide or provided as a complex with the targeting peptide. Thus, the therapeutic agent may be a polypeptide or a nucleic acid. Thus, the following alternatives of therapeutic agent are possible:

The therapeutic agent is a polypeptide which is associated to the targeting peptide by a covalent bond.

The therapeutic agent is a polypeptide and forms a fusion protein with the targeting peptide.

The therapeutic agent is a polynucleotide which may be directly attached to the targeting peptide or by an additional protein domain which shows affinity for DNA, particularly by electrostatic interaction. Suitable protein domains which are capable of associating with DNA via electrostatic interaction include, without limitation, polylysine, protamine, albumin and cationized albumin.

The therapeutic agent is a small organic molecule.

The therapeutic agent is any of the above (polypeptide, polynucleotide or small organic molecule) which is provided within a nanotransporter which is coupled to the targeting peptide.

In a preferred embodiment, the therapeutic agent is a high molecular weight compound. As used herein, "high molecular weight compound" refers to any chemical entity or molecule, such as nucleic acids, peptides, proteins, natural and synthetic polymers, drugs such as antibiotics and the like, having a molecular weight greater than 1 kDa, preferably greater than 5 kDa, more preferably greater than 10 kDa and even more preferably greater than 100 kDa.

B.1. Polypeptides as Therapeutic Agents

In a preferred embodiment, the therapeutic agent is a polypeptide.

The term "polypeptide", as used herein, refers to a polymer of amino acid residues. The term also apply to amino acid polymers in which one or more amino acid residue is an artificial chemical mimetic of a corresponding naturally occurring amino acid, as well as to naturally occurring amino acid polymers and non-naturally occurring amino acid polymer.

In the case that the therapeutic agent is a polypeptide, the conjugate may be a covalent complex of the therapeutic agent and the targeting peptide. In another embodiment, the therapeutic agent and the targeting peptide form a fusion protein. Preferably, wherein the therapeutic agent is a polypeptide and the first and second component form a fusion protein, then the conjugate is not polyphemusin-1 or polyphemusin-2.

In a preferred embodiment, the polypeptide which acts as active agent or the fusion protein formed by the said polypeptide and the targeting peptide further comprises a tag which may be used for the detection or for the purification of the conjugate using reagents showing specific affinity towards said tags. Adequate detection/purification tags includes hexa-his (metal chelate moiety), hexa-hat GST (glutathione S-tranferase) glutathione affinity, calmodulin-binding peptide (CBP), strep-tag, cellulose binding domain, maltose binding protein, S-peptide tag, chitin binding tag, immuno-reactive epitopes, epitope tags, E2tag, HA epitope tag, Myc epitope, FLAG epitope, AU1 and AU5 epitopes, Glu-Glu epitope, KT3 epitope, IRS epitope, Btag epitope, protein kinase-C epitope, VSV epitope or any other tag as long as the tag does not affect the stability of the conjugate or the targeting capabilities.

Suitable polypeptides that can be used as therapeutic agents include any polypeptide which is capable of promoting a decrease in cell proliferation rates.

B.2. Polynucleotides as Therapeutic Agents

In another embodiment, the therapeutic agent forming part of the conjugates of the invention is a nucleic acid. In cases where the therapeutic agent is a polynucleotide, this is either directly associated to the targeting peptide interactions in those cases wherein the peptide has a net positive charge which allows the formation of electrostatic interactions with the DNA. Alternatively, the targeting peptide may comprise an additional protein domain present in said targeting peptide having a net positive charge and thus, capable of forming electrostatic interactions with the DNA. Suitable protein domains which are capable of associating with DNA via electrostatic interaction include, without limitation, polylysine, protamine, albumin and cationized albumin.

The terms "nucleic acid" and "polynucleotide", as used herein interchangeably, refer to a polymer composed of nucleotide units (ribonucleotides, deoxyribonucleotides, related naturally occurring structural variants and synthetic non-naturally occurring analogs thereof or combinations thereof) linked via phosphodiester bonds, related naturally occurring structural variants and synthetic non-naturally occurring analogs thereof.

The nucleic acids include coding regions and the adequate regulatory signals for promoting expression in the target cells in those cases wherein a defective gene function is to be reinstated in the cell or a silencing nucleic acid wherein the expression of a target gene is to be inhibited.

Generally, nucleic acids containing a coding region will be operably linked to appropriate regulatory sequences. Such regulatory sequence will at least comprise a promoter sequence. As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "tissue specific" promoter is only active in specific types of differentiated cells/tissues. Suitable promoters for expression of the nucleotide sequence encoding the polypeptide from gene therapy vectors include e.g. cytomegalovirus (CMV) intermediate early promoter, viral long terminal repeat promoters (LTRs), such as those from murine moloney leukaemia virus (MMLV) rous sarcoma virus, or HTLV-I, the simian virus 40 (SV 40) early promoter and the herpes simplex virus thymidine kinase promoter.

In those cases wherein the nucleic acid includes a coding region, said coding region is selected from the group consisting of a tumor suppressor gene, a suicide gene or a polynucleotide which is capable of activating the immune response towards a tumor.

Suitable genes or cDNAs are those which encode the cytotoxic, proapoptotic or metastasis-suppressor polypeptides mentioned above in relation to the active agent being a polypeptide.

B.3. Small Organic Molecules as Therapeutic Agents

In general, a "small molecule" refers to a substantially non-peptidic, non-oligomeric organic compound either prepared in the laboratory or found in nature. Small molecules, as used herein, can refer to compounds that are "natural product-like," however, the term "small molecule" is not limited to "natural product-like" compounds. Rather, a small molecule is typically characterized in that it contains several carbon-carbon bonds, and has a molecular weight of less than 1500 g/mol, less than 1250 g/mol, less than 1000 g/mol, less than 750 g/mol, less than 500 g/mol, or less than 250 g/mol, although this characterization is not intended to be limiting for the purposes of the present invention. In certain other embodiments, natural-product-like small molecules are utilized.

Suitable small molecules that can be incorporated in the nanotransporters forming part of the conjugates according to the invention include, without limitation, anti-cancer agents, anti-angiogenic agents, pro-apoptotic and antiretroviral agents.

B.4. Nanotransporters as Therapeutic Agents

The term "nanotransporter", as used herein, relates to a multi-component complex with controlled dimensions, e.g., a diameter or radius on the order of about 1 to about 1000 nanometers that contains a compound of interest.

The nanotransporters according to the invention may include one or more of the active agents (polynucleotide or polypeotides) mentioned above as well as any other cytotoxic agent suitable for decreasing cell proliferation, including small molecules.

Preferred nanotransporters for use in the present invention include nanoparticles, viruses, virus-like particles (VLP), nanoparticles, protein cages and the like.

B.4.i. Nanotransporters Based on Nanoparticles

In another embodiment, the nanotransporters are nanoparticles. Nanoparticles suitable for use in the present invention include lipid nanoparticles as well as polymeric nanoparticles.

Polymeric nanoparticles are formed by a polymeric matrix which is attached to the T22 peptide targeting moiety. Non-limiting examples of biocompatible polymers that may be useful in the polymeric nanoparticules according to the present invention include polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, polyglutamate, dextran, polyanhydrides, polyurethanes, polymethacrylates, polyacrylates or polycyanoacrylates.polydioxanone (PDO), polyhydroxylkanoate, polyhydroxybutyrate, poly(glycerol sebacate), polyglycolide, polylactide, PLGA, polycaprolactone or combinations thereof.

Alternatively, the nanoparticles of the invention may be lipid nanoparticles such as a liposome or a micelle.

Formation of micelles and liposomes from, for example, vesicle-forming lipids, is known in the art. Vesicle-forming lipids refer to lipids that spontaneously form lipid bilayers above their gel-to-liquid crystalline phase transition temperature range. Such lipids typically have certain features that permit spontaneous bilayer formation, such as close to identical cross-section areas of their hydrophobic and hydrophilic portions permitting packing into lamellar phases. Lipids capable of stable incorporation into lipid bilayers, such as cholesterol and its various analogs, can be incorporated into the lipid bilayer during bilayer formation. The vesicle-forming lipids are preferably lipids having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two-hydrocarbon chains are typically between about 14-22 carbon atoms in length, and either saturated or having varying degrees of unsaturation. The above-described lipids and phospholipids whose acyl chains have varying degrees of saturation can be obtained commercially or prepared according to published methods. Other suitable lipids include phospholipids, sphingolipids, glycolipids, and sterols, such as cholesterol.

The term "liposome" refers to vesicles comprised of one or more concentrically ordered lipid bilayers, which encapsulate an aqueous phase. The aqueous phase typically contains the compound to be delivered to a target site. Upon reaching a target site, the liposome fuses with the plasma membranes of local tumor cells or tumor blood vessel cells, thereby releasing the compound into the cytosol. Alternatively, the liposome is endocytosed or otherwise taken in by the tumor cells or of tumor blood vessel cells as the content of a transport vesicle (e.g., an endosome or phagosome). Once in the transport vesicle, the liposome either degrades or fuses with the membrane of the vesicle and releases its contents. A variety of methods known to the skilled person are available for preparing liposomes, such as Suitable methods include, for example, sonication, extrusion, high pressure/homogenization, micro fluidization, detergent dialysis, calcium-induced fusion of small liposome vehicles and ether fusion methods, all of which are well known in the art.

Polymeric and lipidic nanotransporters can additionally include a coating of an amphiphilic compound that surrounds the polymeric material forming a shell for the particle or a stealth material that can allow the particles to evade recognition by immune system components and increase particle circulation half life.

B.4.ii. Viral Nanotransporters

In one embodiment, the nanotransporter of the invention is a virus. The skilled person will appreciate that any virus known in the art may be used as nanotransporter in the present invention provided that sufficient information is available so as to allow the modification of the external components by T22 peptide or the functionally equivalent variant thereof. Thus, in the case of non-enveloped viruses, the nanotransporters of the invention are obtained by directly modifying at least one of the capsid proteins, either by chemical coupling of the T22 peptide or the functionally equivalent variant thereof or by inserting the sequence encoding the T22 peptide or the functionally equivalent variant thereof into the viral gene coding for the capsid protein so that, upon synthesis and assembly into the capsid, the T22 peptide or the functionally equivalent variant thereof is exposed to the outer surface of the capsid. Examples of suitable virus capsids that can be modified in the above manner include, but are not limited to, capsids from Sindbis virus and other alphaviruses, rhabdoviruses (e.g. vesicular stomatitis virus), picornaviruses (e.g., human rhino virus, Aichi virus), togaviruses (e.g., rubella virus), orthomyxoviruses (e.g., Thogoto virus, Batken virus, fowl plague virus), polyomaviruses (e.g., polyomavirus BK, polyomavirus JC, avian polyomavirus BFDV), parvoviruses, rotaviruses, bacteriophage Qβ, bacteriophage P1, bacteriophage M13, bacteriophage MS2, bacteriophage G4, bacteriophage P2, bacteriophage P4, bacteriophage 186, bacteriophage Φ6, bacteriophage Φ29, bacteriophage MS2, bacteriophage N4, bacteriophage ΦX174, bacteriophage AP205, Norwalk virus, foot and mouth disease virus, a retrovirus, Hepatitis B virus, Tobacco mosaic virus (TMV), satellite panicum mosaic virus (SPMV), flock house virus and human papilomavirus.

Alternatively, wherein the nanotransporter is an enveloped virus, the targeting peptide is preferably attached to or replacing a part of the envelope glycoproteins. Some non-limiting examples of surface glycoproteins that may be used for inserting the short fiber protein include glycoproteins from alphaviruses, such as Semliki Forest virus (SFV), Ross River virus (RRV) and Aura virus (AV), which comprise surface glycoproteins such as E1, E2, and E3. The E2 glycoproteins derived from the Sindbis virus (SIN) and the hemagglutinin (HA) of influenza virus are non-retroviral glycoproteins that specifically bind particular molecules on cell surfaces (heparin sulfate glycosaminoglycan for E2, sialic acid for HA) which are known to tolerate certain genetic modifications and remain efficiently assembled on the retroviral surface (Morizono et al. J. Virol. 75, 8016-8020); glycoproteins of Lassa fever virus, Hepatitis B virus, Rabies virus, Borna disease virus, Hantaan virus, or SARS-CoV; flavivirus-based surface glycoproteins, hemagglutinin (HA) from influenza A/fowl plague virus/Rostock/34 (FPV), a class I fusogen, is used (T. Hatziioannou, S. Valsesia-Wittmann, S. J. Russell, F. L. Cosset, J. Virol. 72, 5313 (1998)). Suitables viruses for use in the present invention comprise alphaviruses, paramyxoviruses, rhabdoviruses, coronaviruses, picornaviruses, myxoviruses, reoviruses, bunyaviruses, flaviviruses, rubiviruses, filoviruses, arenaviruses, arteriviruses or caliciviruses.

B. 4.iii. Nanotransporters Based on VLPs

In one embodiment, the nanotransporter used in the present invention is a VLP. The term "VLP or viral-like particle", as used herein, relates to a self-assembling macromolecular structure formed by the viral nucleocapsids which acquire a quaternary structure resembling that of the virus from which they originate but which are devoid of the virus genetic material.

The VLPs for use according to the present invention may be formed from polypeptides derived from any virus known in the art having an ordered and repetitive structure. VLPs can be produced and purified from virus-infected cell culture. The resulting virus or virus-like particle for vaccine purpose needs to be devoid of virulence. Besides genetic engineering, physical or chemical methods can be employed to inactivate the viral genome function, such as UV irradiation, formaldehyde treatment. Alternatively, the VLP is a recombinant VLP. The skilled person will appreciate that almost all commonly known viruses of known sequence may be used for the generation of VLPs provided that the gene encoding the coat protein or proteins can be easily identified by a skilled artisan. The preparation of VLPs by the recombinant expression of the coat protein or proteins in a host is within the common knowledge of a skilled artisan. Suitable VLPS can be obtained from the nucleocapsid proteins of a virus selected form the group consisting of RNA-bacteriophages, adenovirus, papaya mosaic virus, influenza virus, norovirus, papillomavirus, hepadnaviridae, respiratory syncytial virus, hepatitis B virus, hepatitis C virus, measles virus; Sindbis virus; rotavirus, foot-andmouth-disease virus, Newcastle disease virus, Norwalk virus, alphavirus; SARS, paramoxyvirus, transmissible gastroenteritis virus retrovirus, retrotransposon Ty, Polyoma virus; tobacco mosaic virus; Flock House Virus, Cowpea Chlorotic Mottle Virus; a Cowpea Mosaic Virus; and alfalfa mosaic virus.

B.4.iv. Nanotransporters Based on Protein Cages

In another embodiment, the nanotransporter used in the present invention is a protein cage. The term "protein cage", as used herein, relates to self-assembling macromolecular structure formed by one or more different proteins which are capable of forming a constrained internal environment. Protein cages can have different core sizes, ranging from 1 to 30 nm (e.g., the internal diameter of the shells). Preferred protein cages suitable for use in the present invention include ferritin protein cages, heat-shock protein cages as described in WO08124483 and the like.

C. Linker Regions

The conjugates object of the invention comprising the targeting peptide and the therapeutic agent wherein said therapeutic agent has a peptidic nature can contain a bond directly connecting the targeting peptide and the therapeutic agent or, alternatively, can contain an additional amino acid sequence acting as a linker between the targeting peptide and the therapeutic agent. The linker peptide preferably comprises at least two amino acids, at least three amino acids, at least five amino acids, at least ten amino acids, at least 15 amino acids, at least 20 amino acids, at least 30 amino acids, at least 40 amino acids, at least 50 amino acids, at least 60 amino acids, at least 70 amino acids, at least 80 amino acids, at least 90 amino acids or approximately 100 amino acids.

According to the invention, said non-natural intermediate amino acid sequence acts as a hinge region between domains, allowing them to move independently from one another while they maintain the three-dimensional shape of the individual domains. In this sense, a preferred non-natural intermediate amino acid sequence according to the invention would be a hinge region characterized by a structural ductility allowing this movement. In a particular embodiment, said non-natural intermediate amino acid sequence is a non-natural flexible linker. In a preferred embodiment, said flexible linker is a flexible linker peptide with a length of 20 amino acids or less. In a more preferred embodiment, the linker peptide comprises 2 amino acids or more selected from the group consisting of glycine, serine, alanine and threonine. In a preferred embodiment of the invention, said flexible linker is a polyglycine linker.

Preferred examples of spacer or linker peptides include those which have been used for binding proteins without substantially deteriorating the function of the bound proteins or at least without substantially deteriorating the function of one of the bound proteins. More preferably, the spacers or linkers have been used for binding proteins comprising structures with coiled helixes such as:

the peptide GTKVHMK (SEQ ID NO:18) formed by residues 53-56 and residues 57-59 of tetranectin (Nielsen, B.B. et al., FEBS Lett. 412: 388-396, 1997);

the connecting strand 3 from human fibronectin, corresponding to amino acids 1992-2102 (SWISSPROT numbering, entry P02751).

The subsequence PGTSGQQPSVGQQ (SEQ ID NO: 19) corresponding to amino acids number 2037-2049 of fibronectin and within that subsequence fragment GTSGQ (SEQ ID NO: 20) corresponding to amino acids 2038-2042.

The 10 amino acid residue sequence of the upper hinge region of murine IgG3 (PKPSTPPGSS, SEQ ID NO: 21). In a preferred embodiment, the linker peptide is selected from the group of the peptide of sequence APAETKAEPMT (SEQ ID NO: 22) and of the peptide of sequence GAP.

The eight amino acid sequence GGSSRSSS (SEQ ID NO:32).

Alternatively, the two components of the conjugates of the invention can be connected by a peptide the sequence of which contains a cleavage target for a protease, thus allowing the separation of the targeting peptide from the therapeutic agent. Protease cleavage sites suitable for their incorporation into the polypeptides of the invention include enterokinase (cleavage site DDDDK, SEQ ID NO: 23), factor Xa (cleavage site IEDGR, SEQ ID NO: 24), thrombin (cleavage site LVPRGS, SEQ ID NO: 25), TEV protease (cleavage site ENLYFQG, SEQ ID NO: 26), PreScission protease (cleavage site LEVLFQGP, SEQ ID NO: 27), inteins and the like.

D. Polynucleotides, Vectors and Host Cells

In those cases wherein the conjugate is a fusion protein of the targeting peptide and the active (therapeutic or diagnostic) agent, then the fusion protein can be produced in vivo by the recipient subject when a polynucleotide encoding the fusion protein is used. Thus, in another aspect, the invention relates to a polynucleotide encoding a conjugate according to the invention.

The expressions "nucleotide sequence", "nucleic acid" and "polynucleotide" are used interchangeably in this invention to refer to the polymer form of phosphate esters of ribonucleosides (adenosine, guanosine, uridine or cytidine; "RNA molecules") or deoxyribonucleosides (deoxyadenosine, deoxyguanosine, deoxythymidine or deoxycytidine; "DNA molecules"), or any analogous phosphoester thereof, such as phosphorothioates and thioesters, in single-strand or double-strand form. Thus, helices formed by DNA-DNA, DNA-RNA and RNA-RNA are possible. The term "nucleic acid sequence" and, in particular, DNA or RNA molecule, refers solely to the primary or secondary structure of the molecule and does not limit any particular type of tertiary structure. Thus, this term includes double-chain DNA as it appears in linear or circular DNA molecules, supercoiled DNA plasmids and chromosomes.

In another aspect, the invention relates to a vector comprising a polynucleotide according to the invention.

As used in this invention, the term "vector" refers to a vehicle whereby a polynucleotide or a DNA molecule may be manipulated or introduced into a cell. The vector may be a linear or circular polynucleotide, or it may be a larger-size polynucleotide or any other type of construct, such as DNA or RNA from a viral genome, a virion or any other biological construct that allows for the manipulation of DNA or the introduction thereof into the cell. It is understood that the expressions "recombinant vector" and "recombinant system" may be used interchangeably with the term "vector". Those skilled in the art will note that there is no limitation in terms of the type of vector that may be used, since said vector may be a cloning vector suitable for propagation and to obtain the adequate polynucleotides or gene constructs or expression vectors in different heterologous organisms suitable for the purification of the conjugates. Thus, suitable vectors in accordance with this invention include expression vectors in prokaryotes, such as pUC18, pUC19, Bluescript and the derivatives thereof, mp18, mp19, pBR322, pMB9, CoIE1, pCR1, RP4, phages and "shuttle" vectors, such as pSA3 and pAT28, expression vectors in yeasts, such as vectors of the 2-micron plasmid type, integration plasmids, YEP vectors, centromere plasmids and similar ones, expression vectors in insect cells, such as the vectors in the pAC series and the pVL series, expression vectors in plants, such as vectors from the pIBI, pEarleyGate, pAVA, pCAMBIA, pGSA, pGWB, pMDC, pMY, pORE series and similar ones, and expression vectors in higher eukaryotic cells based on viral vectors (adenoviruses, viruses associated with adenoviruses, as well as retroviruses and lentiviruses) and non-viral vectors, such as pSilencer 4.1-CMV (Ambion), pcDNA3, pcDNA3.1/hyg, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1.

The vector of the invention may be used to transform, transfect or infect cells susceptible to being tranformed, transfected or infected by said vector.

Therefore, another aspect of the invention relates to a cell that comprises a polynucleotide, a gene construct or a vector of the invention; to this end, said cell has been transformed, transfected or infected with a construct or vector provided by this invention. Transformed, transfected or infected cells may be obtained by conventional methods known to those skilled in the art (Sambrook et al., 2001, cited supra). In a particular embodiment, said host cell is an animal cell transfected or infected with an appropriate vector.

Host cells suitable for the expression of the conjugates of the invention include, without being limited thereto, cells from mammals, plants, insects, fungi and bacteria. Bacterial cells include, without being limited thereto, cells from Gram-positive bacteria, such as species from the genera *Bacillus, Streptomyces* and *Staphylococcus*, and cells from Gram-negative bacteria, such as cells from the genera *Escherichia* and *Pseudomonas*. Fungi cells preferably include cells from yeasts such as *Saccharomyces, Pichia pastoris* and *Hansenula polymorpha*. Insect cells include, without limitation, *Drosophila* cells and Sf9 cells. Plant cells include, amongst others, cells from cultivated plants, such as cereals, medicinal plants, ornamental plants or bulbs. Mammalian cells suitable for this invention include epithelial cell lines (porcine, etc.), osteosarcoma cell lines (human, etc.), neuroblastoma cell lines (human, etc.), epithelial carcinomas (human, etc.), glial cells (murine, etc.), hepatic cell lines (from monkeys, etc.), CHO (Chinese Hamster Ovary) cells, COS cells, BHK cells, HeLa, 911, AT1080, A549, 293 or PER.C6 cells, human NTERA-2 ECC cells, D3 cells from the mESC line, human embryonary stem cells, such as HS293 and BGV01, SHEF1, SHEF2 and HS181, NIH3T3, 293T, REH and MCF-7 cells, and hMSC cells.

E. Conjugates of the Invention Comprising Antitumor Agents and Uses Thereof for the Treatment of Cancer The efficient and specific interaction of the conjugates of the invention with CXCR4+ cells allows the use of said conjugates for the treatment of any disease wherein it is desirable to deliver a compound of interest to cells expressing CXCR4. Thus, in another aspect, the invention relates to a conjugate, a polynucleotide, or a vector according to the invention wherein the therapeutic agent is an antitumor agent.

The term "antitumor agent", as used herein, refers to any chemical or biological agent or compound with antiproliferative, antioncogenic and/or carcinostatic properties which can be used to inhibit tumor growth, proliferation and/or development Suitable antitumor agents for use in the present invention include, without limitation:
(i) a cytotoxic polypeptide,
(ii) an antiangiogenic polypeptide,
(iii) a polypeptide encoded by a tumor suppressor gene,
(iv) a polypeptide encoded by a polynucleotide which is capable of activating the immune response towards a tumor,
(v) a tumor suppressor gene,
(vi) a silencing agent,
(vii) a suicide gene,
(viii) a polynucleotide which is capable of activating the immune response towards a tumor,
(ix) a chemotherapy agent and
(x) an antiangiogenic molecule.

E.1. Cytotoxic Polypeptides

As used herein, the term cytotoxic polypeptide refers to an agent that is capable of inhibiting cell function. The agent may inhibit proliferation or may be toxic to cells. Any polypeptide that when internalized by a cell interfere with or detrimentally alter cellular metabolism or in any manner inhibit cell growth or proliferation are included within the ambit of this term, including, but are not limited to, agents whose toxic effects are mediated when transported into the cell and also those whose toxic effects are mediated at the cell surface. Useful cytoxic polypeptides include proteinaceous toxins and bacterial toxins.

Examples of proteinaceous cell toxins useful for incorporation into the conjugates according to the invention include, but are not limited to, type one and type two ribosome inactivating proteins (RIP). Useful type one plant RIPs include, but are not limited to, dianthin 30, dianthin 32, lychnin, saporins 1-9, pokeweed activated protein (PAP), PAP II, PAP-R, PAP-S, PAP-C, mapalmin, dodecandrin, bryodin-L, bryodin, Colicin 1 and 2, luffin-A, luffin-B, luffin-S, 19K-protein synthesis inhibitory protein (PSI), 15K-PSI, 9K-PSI, alpha-kirilowin, beta-kirilowin, gelonin, momordin, momordin-II, momordin-Ic, MAP-30, alpha-momorcharin, beta-momorcharin, trichosanthin, TAP-29, trichokirin; barley RIP; flax RIP, tritin, corn RIP, Asparin 1 and 2 (Stirpe et al., Bio/Technology 10:405-12, 1992). Useful type two RIPs include, but are not limited to, volkensin, ricin, nigrin-b, CIP-29, abrin, modeccin, ebulitin-[beta], ebultin-[gamma], vircumin, porrectin, as well as the biologically active enzymatic subunits thereof (Stirpe et al., Bio/Technology 10:405-12, 1992; Pastan et al., Annu. Rev. Biochem. 61:331-54; Brinkmann and Pastan, Biochim. et Biophys. Acta 1198:27-45, 1994; and Sandvig and Van Deurs, Physiol. Rev. 76:949-66, 1996).

Examples of bacterial toxins useful as cell toxins include, but are not limited to, shiga toxin and shiga-like toxins (i.e., toxins that have the same activity or structure), as well as the catalytic subunits and biologically functional fragments thereof. These bacterial toxins are also type two RIPs (Sandvig and Van Deurs, Physiol. Rev. 76:949-66, 1996; Armstrong, J. Infect. Dis., 171:1042-5, 1995; Kim et al., Microbiol. Immunol. 41:805-8, 1997, and Skinner et al., Microb. Pathog. 24:117-22, 1998). Additional examples of useful bacterial toxins include, but are not limited to, Pseudomonas exotoxin and Diphtheria toxin (Pastan et al., Annu. Rev. Biochem. 61:331-54; and Brinkmann and Pastan, Biochim. et Biophys. Acta 1198:27-45, 1994). Truncated forms and mutants of the toxin enzymatic subunits also can be used as a cell toxin moiety (Pastan et al., Annu. Rev. Biochem. 61:331-54; Brinkmann and Pastan, Biochim. et Biophys. Acta 1198:27-45, 1994; Mesri et al., J. Biol. Chem. 268:4852-62, 1993; Skinner et al., Microb. Pathog. 24:117-22, 1998; and U.S. Pat. No. 5,082,927). Other targeted agents include, but are not limited to the more then 34 described Colicin family of RNase toxins which include colicins A, B, D, E1-9, cloacin DF13 and the fungal RNase, [alpha]-sarcin (Ogawa et al. Science 283: 2097-100, 1999;

Smarda et al., Folia Microbiol (Praha) 43:563-82, 1998; Wool et al., Trends Biochem. Sci., 17: 266-69, 1992).

E. 2. Antiangiogenic Peptides and Polypeptides

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment.

The term "anti-angiogenic polypeptide", as used herein, denotes a polypeptide capable of inhibiting angiogenesis. Suitable antiangiogenic polypeptides include, without limitation, angiostatin, endostatin, anti-angiogenic anti-thrombin III, sFRP-4 as described in WO2007115376, an anti-VEGF antibody such as anibizumab, bevacizumab (avastin), Fab IMC 1121 and F200 Fab.

E. 3. Polypeptides Encoded by Tumor Suppressor Genes,

As used herein, a "tumor suppressor" is a gene or gene product that has a normal biological role of restraining unregulated growth of a cell. The functional counterpart to a tumor suppressor is an oncogene. Genes that promote normal cell growth may be known as "protooncogenes". A mutation that activates such a gene or gene product further converts it to an "oncogene", which continues the cell growth activity, but in a dysregulated manner. Examples of tumor suppressor genes and gene products are well known in the literature and may include PTC, BRCA1, BRCA2, p16, APC, RB, WT1, EXT1, p53, NF1, TSC2, NF2, VHL, ST7, ST14, PTEN, APC, CD95 or SPARC.

E.4. Pro-Apoptotic Polypeptides

The term "pro-apoptotic polypeptides", as used herein, refers to a protein which is capable of inducing cell death in a cell or cell population. Suitable pro-apoptotic polypeptides include, without limitation, proapoptotic members of the BCL-2 family of proteins such as BAX, BAK, BOK/MTD, BID, BAD, BIK/NBK, BLK, HRK, BIM/BOD, BNIP3, NIX, NOXA, PUMA, BMF, EGL-I, and viral homologs, caspases sich as caspase-8, the adenovirus E4orf4 gene, p53 pathway genes, proapoptotic ligands such as TNF, FasL, TRAIL and/or their receptors, such as TNFR, Fas, TRAIL-R1 and TRAIL-R2.

E.5. Polypeptides Having Anti-Metastatic Activity

The term "metastasis suppressor" as used herein, refers to a protein that acts to slow or prevent metastases (secondary tumors) from spreading in the body of an organism with cancer. Suitable metastasis suppressors include, without limitation, proteins such as BRMS 1, CRSP3, DRG1, KAI1, KISS-1, NM23, a TIMP-family protein and uteroglobin.

E. 6. Immunostimulatory Polypeptides

As used herein, an immunostimulatory polypeptide agent is a polypeptide that stimulates an immune response (including enhancing a pre-existing immune response) in a subject to whom it is administered, whether alone or in combination with another agent, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

E. 7. Tumor Suppressor Genes

Suitable tumor suppressor genes include a gene or gene product that encodes any of the polypeptides defined above. Examples of tumor suppressor genes and gene products are well known in the literature and may include PTC, BRCA1, BRCA2, p16, APC, RB, WT1, EXT1, p53, NF1, TSC2, NF2, VHL,ST7, ST14, PTEN, APC, CD95 or SPARC.

E. 8. Silencing Agents

Wherein the nucleic acid is a silencing agent, said silencing agent is aimed at blocking the expression of genes the over-expression of which leads to cell proliferation and tumor growth. Genes that can be inhibited by the conjugates according to the invention carrying silencing agent include, without limitation, HRAS (v-Ha-ras Harvey rat sarcoma viral oncogene homolog), NRAS (neuroblastoma RAS viral (v-ras) oncogene homolog), KRAS (v-Ki-ras2 Kirsten rat sarcoma viral oncogene homolog), MYC (v-myc myelocytomatosis viral oncogene homolog, avian), MYCN (v-myc myelocytomatosis viral related oncogene, neuroblastoma derived, avian), MYB (v-myb myeloblastosis viral oncogene homolog, avian), Jun-oncogene, FOS (v-fos FBJ murine osteosarcoma viral oncogene homolog), Oncogenic ABL1 (v-abl Abelson murine leukemia viral oncogene homolog 1 (this gene is an oncogene only if the SH3 domain is truncated, as happens regularity in certain leukemias), SRC (v-src sarcoma (Schmidt-Ruppin A-2) viral oncogene homolog, avian), FES (Feline sarcoma oncogene), RAF1(v-raf-1 murine leukemia viral oncogene homolog 1), REL (v-rel reticuloendotheliosis viral oncogene homolog, avian), RELA (v-rel reticuloendotheliosis viral oncogene homolog A, nuclear factor of kappa light polypeptide gene enhancer in B-cells 3, p65, avian), RELB (v-rel reticuloendotheliosis viral oncogene homolog B, nuclear factor of kappa light polypeptide gene enhancer in B-cells 3, avian), FGR (Gardner-Rasheed feline sarcoma viral (v-fgr) oncogene homolog), and KIT (v-kit Hardy-Zuckerman 4 feline sarcoma viral oncogene homolog).

Other silencing agents suitable for use in the present invention include those directed against cyclin G1, cyclin D1, Bcl-2 (B-cell chronic lymphatic leukemia associated protein 2), Bcl-XL (Bcl-2 related gene xl), HLA-G (Human leukocyte antigen class G), IGF-1 (Insulin-like growth factor-1), EGF (epidermal growth factor), FGF (fibroblast growth factor), VEGF (vascular endothelial growth factor), VEGFR (vascular endothelial growth factor receptor), IGFR (insulin-like growth factor receptor), EGFR (epidermal growth factor receptor), FGFR (fibroblast growth factor receptor), TGF-beta (transforming growth factor beta), Caspase 3, CEACAM6 (Carcinoembryonic antigen-related cell adhesion molecule 6), HPV-E6 (human papiloma virus protein E6), HPV-E7 (human papiloma virus protein E7), H-Ras gene, P100a gene, CREB (cAMP response element binding), BRAF gene, ATF2 (activating transcription factor 2), HER2 (Human EGF-like Receptor No. 2), and N-myc.

Examples of therapeutic molecules include, but are not limited to, cell cycle control agents; agents which inhibit cyclin proteins, such as antisense polynucleotides to the cyclin G1 and cyclin D1 genes.

In another embodiment, the silencing agent can be targeted against CXCR4. Suitable CXCR4-silencing agents include, without limitation:

The antisense oligonucleotides to CXCR4 having the sequences 5'-CTGATCCCCTCCATGGTAACCGCT-3' (SEQ ID NO: 10), 5'-TATATACTGATCCCCTC-CATGGTA-3' (SEQ ID NO: 11) and 5-CCTC-CATGGTAACCGCTGGTTCT-3' (SEQ ID NO: 12) and described in U.S. Pat. No. 6,429,308;

The CXCR4-specific siRNAs as described in WO2008008852 comprising sense strands having the sequences 5'-UAAAAUCUUCCUGCCCACCdTdT-3' (SEQ ID NO: 13) and 5'-GGAAGCU-GUUGGCUGAAAAdTdT-3' (SEQ ID NO: 14).

The CXCR4-specific interference RNAs targeting the sequences within CXCR4 mRNA described in WO2007143584.

The CXCR4-specific interference RNAs targeting the sequences within CXCR4 mRNA described in US20050124569.

The CXCR4-specific ribozyme having the sequence 3'-UGUUGCA-X-Y-X-UCACUC-5' wherein X are the catalytic sequences and Y is the sequence of a stem-loop region. Detailed structures of this ribozyme and the DNA-cassetes encoding said sequences are described in U.S. Pat. No. 6,916,653;

The CXCR4-specific shRNA having the sequence 5'-GATCCAGGATGGTGGTGTTTCAATTCCTT-CAAGAGAGGAATTGAAACACCACCA TCCTTTTTGG-3 (SEQ ID NO: 15) as described in US2009210952.

The CXCR4-specific siRNAs targeting the sequences within the CXCR4 mRNA AATAAAATCTTCCTGCC-CACC (SEQ ID NO: 16) and AAGGAAGCTGTTGGCTGAAAA (SEQ ID NO: 17) as described in WO2004087068.

The CXCR4-specific interference RNAs targeting the sequences within CXCR4 mRNA described in US2009235772 and US2005124569.

Potential target sites in the mRNA for the design of RNA-interference agents are identified based on rational design principles, which include target accessibility and secondary structure prediction. Each of these may affect the reproducibility and degree of knockdown of expression of the mRNA target, and the concentration of siRNA required for therapeutic effect. In addition, the thermodynamic stability of the siRNA duplex (e.g., antisense siRNA binding energy, internal stability profiles, and differential stability of siRNA duplex ends) may be correlated with its ability to produce RNA interference. (Schwarz et al., Cell 115:199-208, 2003; Khvorova et al., Cell 115:209-216, 2003). Empirical rules, such as those provided by the Tuschl laboratory (Elbashir et al., Nature 411:494-498, 2001; Elbashir et al., Genes Dev. 15:188-200, 2001) are also used. Software and internet interactive services for siRNA design are available at the Ambion and Invitrogen websites. Levenkova et al. describe a software system for design and prioritization of siRNA oligos (Levenkova et al., Bioinformatics 20:430-432, 2004). The Levenkova system is available on the internet and is downloadable freely for both academic and commercial purposes. The siRNA molecules disclosed herein were based on the Ambion, Invitrogen and Levenkova recommendations.

Typically, siRNA oligos specific for a given target is carried out based primarily on uniqueness vs. human sequences (i.e., a single good hit vs human Unigene, and a big difference in hybridization temperature Tm against the second best hit) and on GC content (i.e., sequences with percent GC in the range of 40-60 percent). Optionally, for a more detailed picture on the potential hybridization of the oligos, RNA target accessibility and secondary structure prediction can be carried out using, for example, Sfold software (Ding Y and Lawrence, C. E. (2004) Rational design of siRNAs with Sfold software. In: RNA Interference: from Basic Science to Drug Development. K. Appasani (Ed.), Cambridge University Press; Ding and Lawrence, Nucleic Acids Res. 29:1034-1046, 2001; Nucleic Acids Res. 31:7280-7301, 2003). Sfold is available on the internet. RNA secondary structure determination is also described in Current Protocols in Nucleic Acid Chemistry, Beaucage et al., ed, 2000, at 11.2.1-11.2.10.

The type and mode of action of the silencing agent is not particularly limiting in the context of the present invention. Suitable silencing agents include, without limitation, antisense RNA or DNA, ribozymes and other oligonucleotides that are intended to be used as antisense agents. Suitable silencing agents against a gene of interest can be identified using standard techniques to detect expression levels of a gene, such as RT-PCR, Northern blot and the like.

Antisense oligonucleotides, including, antisense oligonucleotides; triplex molecules; dumbbell oligonucleotides; Extracellular Protein Binding Oligonucleotides; and Small Nucleotide Molecules, are oligonucleotides that specifically bind to mRNA that has complementary sequences, thereby preventing translation of the mRNA (see, e.g., U.S. Pat. No. 5,168,053 to Altman et al. U.S. Pat. No. 5,190,931 to Inouye, U.S. Pat. No. 5,135,917 to Burch; U.S. Pat. No. 5,087,617 to Smith and Clusel et al. (1993) Nucl. Acids Res. 21:3405-3411, which describes dumbbell antisense oligonucleotides). Triplex molecules refer to single DNA strands that target duplex DNA and thereby prevent transcription (see, e.g., U.S. Pat. No. 5,176,996 to Hogan et al. which describes methods for making synthetic oligonucleotides that bind to target sites on duplex DNA).

E.9. Suicide Genes

In another embodiment, the polynucleotide used as active agent comprises the coding region of a suicide gene. The term "suicide gene" refers to a nucleic acid coding for a product, wherein the product causes cell death by itself or in the presence of other compounds. A representative example of a suicide gene is one, which codes for thymidine kinase of herpes simplex virus. Additional examples are thymidine kinase of varicella zoster virus and the bacterial gene cytosine deaminase, which can convert 5-fluorocytosine to the highly cytotoxic compound 5-fluorouracil.

Suicide genes may produce cytotoxicity by converting a prodrug to a product that is cytotoxic. In one embodiment, the term "prodrug" means any compound that can be converted to a toxic product for cells. A representative example of such a prodrug is gancyclovir which is converted in vivo to a toxic compound by HSV-thymidine kinase.

The gancyclovir derivative subsequently is toxic to cells. Other representative examples of prodrugs include acyclovir, FIAU [1-(2-deoxy-2-fluoro-beta-D-arabinofuranosyl)-5-iodouracil], 6-methoxypurine arabinoside for VZV-TK, and 5-fluorocytosine for cytosine deaminase.

E.10. Polynucleotides Capable of Activating the Immune Response Towards a Tumor

Suitable polynucleotides capable of activating the immune response towards a tumor include a gene that encodes any immunostimulatory polypeptide agent as defined above.

E.11. Chemotherapy Agents

As used herein, an anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids, or epipodophyllotoxins.

Examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRES SA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLLM1D, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil; Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7-trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2'',5''-dihydroxyphenyl)ethane, or HDBA (2-Hydroxy5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 ($C_{23}H_{24}O_8$), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-Al2 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin. The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia,), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), I0R-C5, 10R-T6 (anti-CD 1), IOR EGF/R3, celogovab (ONCOSCINT OV 103), epratuzumab (LYMPHOCIDE), pemtumomab (THERAGYN), and Gliomab-H (indicated for brain cancer, melanoma).

Other suitable active agents are DNA cleaving agents. Examples of DNA cleaving agents suitable for inclusion as the cell toxin in the conjugates used in practicing the methods include, but are not limited to, anthraquinone-oligopyrrol-carboxamide, benzimidazole, leinamycin; dynemycin A; enediyne; as well as biologically active analogs or derivatives thereof (i.e., those having a substantially equivalent biological activity). Known analogs and derivatives are disclosed, for examples in Islam et al., J. Med. Chem. 34 2954-61, 1991; Skibo et al., J. Med. Chem. 37:78-92, 1994; Behroozi et al., Biochemistry 35:1568-74, 1996; Helissey et al., Anticancer Drug Res. 11:527-51, 1996; Unno et al., Chem. Pharm. Bull. 45:125-33, 1997; Unno et al., Bioorg. Med. Chem., 5:903-19, 1997; Unno et al., Bioorg. Med. Chem., 5: 883-901, 1997; and Xu et al., Biochemistry 37:1890-7, 1998). Other examples include, but are not limited to, endiyne quinone imines (U.S. Pat. No. 5,622,958); 2,2r-bis (2-aminoethyl)-4-4'-bithiazole (Lee et al., Biochem. Mol. Biol. Int. 40:151-7, 1996); epilliticine-salen-.copper conjugates (Routier et al., Bioconjug. Chem., 8: 789-92, 1997).

E.12. Antiangiogenic Molecules

It is contemplated that in certain embodiments of the invention a protein that acts as an angiogenesis inhibitor is targeted to a tumor. These agents include, in addition to the anti-angiogenic polypeptides mentioned above, Marimastat; AG3340; COL-3, BMS-275291, Thalidomide, Endostatin, SU5416, SU6668, EMD121974, 2-methoxyoestradiol, carboxiamidotriazole, CM1O1, pentosan polysulphate, angiopoietin 2 (Regeneron), herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline.

Thus, in another aspect, the invention relates to a conjugate according to the invention for use in medicine. In yet another embodiment, the invention relates to a pharmaceutical composition comprising a conjugate according to the invention and a pharmaceutically acceptable carrier.

As used herein, the term "pharmaceutically acceptable carrier" means a non-toxic, inert solid, semi-solid or liquid filler, diluent, encapsulating material or formulation auxiliary of any type. Remington's Pharmaceutical Sciences. Ed. by Gennaro, Mack Publishing, Easton, Pa., 1995 discloses various carriers used in formulating pharmaceutical compositions and known techniques for the preparation thereof.

The pharmaceutical compositions of this invention can be administered to a patient by any means known in the art including oral and parenteral routes. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

Since CXCR45 is overexpressed in series of tumor cells, the conjugates of the invention are particularly useful for the delivery of compound of interest to said tumor cells. If the active compound has cytostatic or cytotoxic activity, then the conjugates are particularly useful for the treatment of cancers which over-express CXCR4.

Thus, in another aspect, the invention relates to a conjugate according to the invention, a polynucleotide according to the invention, a vector according to the invention or a host cell according to the invention for use in a method for the treatment of cancer wherein said cancer contains cells that expresses CXCR4.

Alternatively, the invention relates to the use of a conjugate according to the invention, a polynucleotide according to the invention, a vector according to the invention or a host cell according to the invention for the manufacture of a medicament for use in a method for the treatment of cancer wherein said cancer contains cells that expresses CXCR4.

Alternatively, the invention relates to a method for the treatment in a subject of cancer wherein said cancer contains cells that expresses CXCR4 comprising the administration to said subject of a conjugate according to the invention, a polynucleotide according to the invention, a vector according to the invention or a host cell according to the invention.

"Cancer containing cells that expresses CXCR4" include, without limitation, ovarian, bladder, colorectal, lung, head and neck, renal, stomach, uterine, acute lymphoblastic leukemia, and cervical cancers. In a preferred embodiment, the cancer to be treated using the method according to the present invention is colorectal cancer or pancreatic cancer.

As used herein, the term "colorectal cancer" includes any type of colon, rectal and appendix neoplasia and refers both to early and late adenomas and to carcinomas as well as to the hereditary, familial or sporadic cancer. Hereditary CRC includes those syndromes which include the presence of polyps, such as the hamartomatous polyposis syndromes and the most known, familial adenomatous polyposis (FAP) as well as nonpolyposis syndromes such as hereditary nonpolyposis colorectal cancer (HNPCC) or Lynch syndrome I.

In a preferred embodiment of the invention, said colorectal cancer (CRC) is colon cancer, rectal cancer and/or vermiform appendix cancer. In another embodiment of the invention, said colorectal cancer is stage 0, stage I, stage II, stage III and/or stage IV colorectal cancer. The stages of CRC referred to herein correspond to the American Joint Committee on Cancer (AJCC) CRC staging, although other staging methods, such as Dukes and Astler-Coller staging, can equally be used.

As used herein, the phrase "pancreatic cancer" refers to a malignant neoplasm of the pancreas, including but not limited to, adenocarcinomas, adenosquamous carcinomas, signet ring cell carcinomas, hepatoid carcinomas, colloid carcinomas, undifferentiated carcinomas, undifferentiated carcinomas with osteoclast-like giant cells and islet cell carcinomas.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

For example, in the case of treating cancer, an enhanced immune response could also be monitored by observing one or more of the following effects: (1) inhibition, to some extent, of tumor growth, including, (i) slowing down (ii) inhibiting angiogenesis and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The agents are administered in effective amounts. An effective amount is a dosage of the agent sufficient to provide a medically desirable result. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment. For example, if the subject has a tumor, an effective amount may be that amount that reduces the tumor volume or load (as for example determined by imaging the tumor). Effective amounts may also be assessed by the presence and/or frequency of cancer cells in the blood or other body fluid or tissue (e.g., a biopsy). If the tumor is impacting the normal functioning of a tissue or organ, then the effective amount may be assessed by measuring the normal functioning of the tissue or organ.

The conjugates are formulated for selected delivery routes including, but are not limited to, topically, intraarticularly, intracisternally, intraocularly, intraventricularly, intrathecally, intravenously, intramuscularly, intratracheally, intraperitoneally and intradermally.

F. Conjugates of the Invention Comprising Antiviral Agents and Uses thereof for the Treatment of Diseases Caused by HIV Infection Since CXCR4 is expressed predominatly in CD4+ cells, the conjugates of the invention are particularly useful for the delivery of compound of interest to said CD4+ cells. If the active compound has anti-retroviral activity or is capable of inducing the death of the cells, the conjugates are particularly useful for the treatment of diseases associated with an HIV infection.

Thus, in another aspect, the invention relates to a conjugate according to the invention, a polynucleotide according to the invention, a vector according to the invention or a host cell according to the invention wherein the therapeutic agent is an antiretroviral agent.

The term "antiretroviral agent" as used herein refers to a compound that inhibits the ability of a retrovirus to effectively infect a host. Antiretroviral agents can inhibit a variety of process including the replication of viral genetic materials, or entry of retroviruses into cells. In some embodiments, antiretroviral agents are selected from the group consisting of: protease inhibitor, a reverse transcriptase inhibitor, and a viral fusion inhibitor.

In a preferred embodiment, the active compound is an anti-HIV agent that can be used for the treatment of a disease associated with HIV infection. Suitable anti-HIV agents for use as therapeutic agents according to the invention include, without limitation, one or more of the following:

1) Combination drugs: efavirenz, emtricitabine or tenofovir disoproxil fumarate (ATRIPLA (R)BMS, Gilead); lamivudine or zidovudine (COMBIVIR (R)/GSK); abacavir or lamivudine (EPZICOM (R)/GSK); abacavir, lamivudine or zidovudine (TRIZIVIR (R)/GSK); emtricitabine, tenofovir disoproxil fumarate (TRUVADA (R)/Gilead).
2) Entry and fusion inhibitors: maraviroc (CELSENTRI (R), SELZENTRY (R)/Pfizer); pentafuside or enfuvirtide (FUZEON (R)/Roche, Trimeris). In some embodiments, the viral entry inhibitor is a fusion inhibitor, a CD4 receptor binding inhibitor, is a CD4 mimic or a gp120 mimic. In some further embodiments, the viral entry inhibitor is a gp41 antagonist, a CD4 monoclonal antibody or a CCR5 antagonist, including CCR5 antagonist sub-classes such as, for example, zinc finger inhibitors. In yet another embodiment, the viral entry inhibitor is a CXCR4 co-receptor antagonist.
3) Integrase inhibitors: raltegravir or MK-0518 (ISENTRESS (R)/Merck).
4) Reverse transcriptase inhibitors: Suitable reverse transcriptase inhibitors for use in the compositions according to the present invention is one or more compounds selected from the group consisting of emtricitabine, capravirine, tenofovir, lamivudine, zalcitabine, delavirdine, nevirapine, didanosine, stavudine, abacavir, alovudine, zidovudine, racemic emtricitabine, apricitabine, emivirine, elvucitabine, TMC-278, DPC-083, amdoxovir, (−)-beta-D-2,6-diamino-purine dioxolane, MIV-210 (FLG), DFC (dexelvucitabine), dioxolane thymidine, Calanolide A, etravirine (TMC-125), L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-$I^2$-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, and L697639, where the compounds are present in amounts effective for treatment of HIV when used in a combination therapy.
5) Protease inhibitors: Suitable protease inhibitors that can be combined with the miRNAs or polynucleotides encoding miRNAs according to the invention is selected from the group consisting of ritonavir, lopinavir, saquinavir, amprenavir, fosamprenavir, nelfmavir, tipranavir, indinavir, atazanavir, TMC-126, darunavir, mozenavir (DMP-450), JE-2147 (AG1776), L-756423, KNI-272, DPC-681, DPC-684, telinavir (SC-52151), BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, and brecanavir (GW640385). Preferred protease inhibitors for use in combination with a compound of the present invention include saquinavir, ritonavir, indinavir, nelfhavir, amprenavir, lopinavir, atazanavir, darunavir, brecanavir, fosamprenavir, and tipranavir. Particularly useful such combinations include, for example, AZT+3TC; TDF+3TC; TDF+FTC; ABC+3TC; and Abacavir+3TC.

Additionally, the compositions according to the present invention may further comprise an antiretroviral agent selected from the group consisting of vaccines, gene therapy treatments, cytokines, TAT inhibitors, and immunomodulators in amounts effective for treatment of HIV when used in a combination therapy.

In another aspect, the invention relates to a conjugate according to the invention, a polynucleotide according to the invention, a vector according to the invention or a host cell according to the invention wherein the therapeutic agent is selected from the group consisting of
  (i) an antiretroviral agent,
  (ii) a cytotoxic polypeptide,
  (iii) a pro-apoptotic polypeptide
  (iv) a silencing agent and
  (v) a suicide gene,
for use in the treatment of a disease associated with a HIV infection.

Alternatively, the invention relates to the use of a conjugate according to the invention, a polynucleotide according to the invention, a vector according to the invention wherein the therapeutic agent is selected from the group consisting of
  (i) an antiretroviral agent,
  (ii) a cytotoxic polypeptide,
  (iii) a pro-apoptotic polypeptide
  (iv) a silencing agent and
  (v) a suicide gene,
for the manufacture of a medicament for use in a method for the treatment.

Alternatively, the invention relates to a method for the treatment of a disease associated with HIV infection in a subject in need thereof which comprises the administration to said subject of a conjugate according to the invention, a polynucleotide according to the invention, a vector according to the invention wherein the therapeutic agent is selected from the group consisting of
  (i) an antiretroviral agent,
  (ii) a cytotoxic polypeptide,
  (iii) a pro-apoptotic polypeptide
  (iv) a silencing agent and
  (v) a suicide gene, The term "retroviral agent" has been defined above.

The terms "cytotoxic polypeptide", "pro-apoptotic polypeptide", "silencing agent" and "suicide gene" have been explained in detail above in the context of the antitumoral agents of the invention and are equally applied in the context of the present methods.

Suitable silencing agents include, without limitation, siRNA constructs for suppression of HIV replication. These siRNA constructs can be specific for various HIV targets (reviewed in Morris (2006) Gene Ther 13:553-558; Rossi (2006) Biotechniques Suppl:25-29; Nekhai (2006) Curr Opin Mol Ther 8:52-61; and Cullen (2005) AIDS Rev 7:22-25). In order to prevent HIV infection of host T-cells, the invention also features components to decrease expression of T cell coreceptors (e.g., CCR5 and CCR4). Such suppression would be expected to hinder infection of host T-cells as people with CCR5A32 mutation are resistant to HIV infection. The invention also features the inclusion of multiple siRNA constructs (e.g., constructs against HIV genes and T-cell receptors used for HIV infection). Here, one siRNA construct can block infection and while a second siRNA construct prevents progression of infection.

The term "disease associated with HIV infection", as used herein, includes a state in which the subject has developed AIDS as well as a state in which the subject infected with HIV has not shown any sign or symptom of the disease. Thus, the compositions of the invention when administered to a subject that has no clinical signs of the infection can have a preventive activity, since they can prevent the onset of the disease. The compositions are capable of preventing or slowing the infection and destruction of healthy CD4+ T cells in such a subject. It also refers to the prevention and slowing the onset of symptoms of the acquired immunodeficiency disease such as extreme low CD4+ T cell count and repeated infections by opportunistic pathogens such as *Mycobacteria* spp., *Pneumocystis carinii*, and *Pneumocystis cryptococcus*. Beneficial or desired clinical results include, but are not limited to, an increase in absolute naïve CD4+ T-cell count (range 10-3520), an increase in the percentage of CD4+T-cell over total circulating immune cells (range 1-50 percent), and/or an increase in CD4+ T-cell count as a percentage of normal CD4+ T-cell count in an uninfected subject (range 1-161 percent). "Treatment" can also mean prolonging survival of the infected subject as compared to expected survival if the subject did not receive any HIV targeted treatment.

The present invention further relates to preventing or reducing symptoms associated with HIV infection. These include symptoms associated with the minor symptomatic phase of HIV infection, including, for example, shingles, skin rash and nail infections, mouth sores, recurrent nose and throat infection and weight loss. In addition, further symptoms associated with the major symptomatic phase of HIV infection, include, for instance, oral and vaginal thrush (Candida), persistent diarrhea, weight loss, persistent cough and reactivated tuberculosis or recurrent herpes infections, such as cold sores (herpes simplex). Other symptoms of full-blown AIDS which can be treated in accordance with the present invention include, for instance, diarrhea, nausea and vomiting, thrush and mouth sores, persistent, recurrent vaginal infections and cervical cancer, persistent generalized lymphadenopathy (PGL), severe skin infections, warts and ringworm, respiratory infections, pneumonia, especially *Pneumocystis carinii pneumonia* (PCP), herpes zoster (or shingles), nervous system problems, such as pains, numbness or "pins and needles" in the hands and feet, neurological abnormalities, Kaposi's sarcoma, lymphoma, tuberculosis or other similar opportunistic infections.

Preparation of the Conjugates of the Invention

Methods for the preparation of the conjugates are provided. These methods include chemical conjugation methods and methods that rely on recombinant production of the conjugates.

The targeting peptide used in the practice of the invention may be attached to the active compound of therapeutic or diagnostic interest by chemical modification. Typically, the chemical methods rely on derivatization of the active agent (therapeutic or diagnostic) with the desired linking agent, and then reaction with the targeting peptide. The chemical methods of derivatization may be carried out using bifunctional cross-linking agents.

In practicing the chemical method, a targeting peptide that is produced by any means, typically by expression of DNA in a bacterial or eukaryotic host or by chemical synthesis is chemically coupled with the active agent. If the targeting peptide or active agent does not contain suitable moieties for effecting chemical linkage it can be derivatized. For example, the agent, such as Shiga toxin, gelonin or other such agent, can be derivatized such as by reaction with a linking agent, such as N-succinimidyl-3-(2-pyridyidithio) propionate (SPDP). In other embodiments, the targeted agent, such as shiga A chain, is modified at or near the N-terminus to include a cysteine residue, so that the resulting modified agent can react with the chemokine receptor-binding moiety protein without further derivatization.

Non-limiting examples of possible chemical groups involved in such the conjugation are: a carboxylic acid group on the targeting peptide, which could be reacted with an amino group on the active agent (for example, the .epsilon.-amino group on a lysine side chain) to form an amide group linking the targeting peptide and the active agent; an amino group on the targeting peptide, which could be reacted with a carboxylic acid group on the active agent (for example, the carboxylic acid group on a glutamate or aspartate side chain) to form an amide group linking the targeting peptide and the active agent; a disulfide group on the targeting peptide, which could be reacted with a thiol group on the active agent (for example, the thiol group on a cysteine side chain) to form a disulfide group linking the targeting peptide and the active agent.

Once conjugated, the conjugate generally will be purified to separate the conjugate from unconjugated targeting agents or from other contaminants. A large number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

In certain embodiments, the conjugate is a fusion protein of the targeting peptide and the therapeutic agent, in which case the fusion protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50 percent, about 60 percent, about 70 percent, about 80 percent, about 90 percent, about 95 percent, or more of the proteins in the composition.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

The invention is described by way of the following examples which are to be construed as merely illustrative and not limitative of the scope of the invention.

EXAMPLES

Materials and Methods
Protein Production and Purification.

GFP fusion genes were produced by standard recombinant DNA technologies, to encode hybrid proteins containing a His tag at the C terminus and a relevant CXCR4 ligand at the amino terminus. The encoded proteins T22-GFP-H6, V1-GFP-H6, vCCL2-GFP-H6 and CXCL12-GFP-H6 (Table 2) were produced in soluble form in *Escherichia coli* strain Origami B (OmpT-, lon-, trxB-, gor-(Novagen)). Bacteria carrying the different pET22b versions (Novagen 69744-3) encoding for each fusion proteins, were grown in Luria-Bertani (LB) medium and protein expression was induced by 0.1 mM isopropyl-β-D-thiogalactopyronaside (IPTG). Bacterial cultures were centrifuged and resuspended in buffer A (20 mM Tris-HCl pH 7.5, 500 mM NaCl, 10 mM Imidazole) in presence of EDTA-free protease inhibitor (Complete EDTA-Free; Roche). The cells were then disrupted by 1100 psi presion using a french press (Thermo FA-078A).

Proteins were purified from crude cell extracts by 6×His tag affinity chromatography using HiTrap Chelating HP 1 ml $Ni^{2+}$ columns (GE healthcare) in an AKTA purifier FPLC (GE healthcare). Positive fractions were collected in elution buffer (Tris-HCl 20 mM pH 7.5, 500 mM NaCl, 500 mM Imidazole), dialyzed against PBS+10% glycerol or 20 mM Tris 500 mM NaCl buffers, and quantified by Bradford's procedure. Protein integrity was characterized by mass spectrometry (MALDI-TOF) and N-terminal sequencing.

DNA Retardation Assays and Transmission Electron Microscopy

DNA-protein incubation and DNA mobility assays were performed according to previously published protocols (2) in PBS pH 6+10% glycerol.

For transmission electron microscopy, purified proteins were diluted to 0.2 mg/ml final concentration. All the protein samples were negatively stained with 2% Uranyl acetate onto carbon coated grids. The samples were also platinated by depositing evaporated 1 nm platinum layer over the sample containing grids. All the samples were visualized in Hitachi H-7000 transmission electron microscope.

Cell Culture and Confocal Laser Scanning Microscopy

HeLa (ATCC-CCL-2) cell line was used in all the experiments and monitored in vivo, in absence of fixation. Cells were maintained in MEM (GIBCO, Rockville, Md.) supplemented with 10% Fetal Calf Serum (GIBCO) and incubated at 37° C. and 5% $CO_2$ in a humidified atmosphere. GFP fusion proteins at the concentrations indicated, were added to cell culture in the presence of Optipro medium (GIBCO, Invitrogen) 20 h before confocal analysis, except for timecourse studies and studies of internalization in the presence of serum (complete media). For confocal analysis, cells were grown on Mat-Teck culture dishes (Mat Teck Corp., Ashland, Mass., United States). Nuclei were labelled with 20 pg/ml Hoechst 33342 (Molecular Probes, Eugene, Oreg., United States) and the plasma membrane was labelled with 2.5 μg/ml CELLMASK Deep Red (Molecular Probes, Invitrogen, Carlsbad, Calif., USA) for 5 min in the dark. Cells were washed in PBS (Sigma-Aldrich Chemie GmbH, Steinheim, Germany). Live cells were recorded with a TCS-SP5 confocal laser scanning microscope (Leica Microsystems, Heidelberg, Germany) using a Plan Apo 63x/1.4 (oil HCxPL APO lambda blue) objective. Hoechst 33342 DNA labels was excited with a blue diode (405 nm) and detected in the 415-460 nm range. GFP-proteins were excited with an Ar laser (488 nm) and detected in the 525-545 nm range. CELLMASK™ was excited with a HeNe laser (633 nm) and detected in the 650-775 nm range. To determine the protein localization inside the cell, stacks of 10 to 20 sections every 0.5 μm along the cell thickness were collected. The projections of the series obtained were generated with Leica LAS AF software, and three-dimensional models were generated using Imaris v. 6.1.0 software (Bitplane; Zürich, Switzerland).

Protein-Mediated Plasmid Transfection

For expression experiments, 20, 40, 60 and 80 μg of T22-GFP-H6 protein (1, 2, 3 and 4 retardation units —RU—) and 1 μg of TdTomato expression vector were mixed into a final volume of 85 μl of PBS+10% glycerol buffer, and complexes were formed after 1 h at room temperature, after which convenient volumes of Optipro were added. The complex was gently added to HeLa cells, followed by incubation for 24 and 48 h at 37° C. in 5% $CO_2$ atmosphere. TdTomato gene expression was monitored by flow cytometry and by confocal microscopy. Cells without treatment, or just incubated with the expression vector or the protein alone, were used as controls.

Flow Cytometry

Cell samples were analyzed after treatment with 0.5 mg/ml trypsin, 4Na in HBSS for 1 min on a FACSCanto system (Becton Dickinson), using a 15 mW air-cooled argon-ion laser at 488 nm excitation. Fluorescence emission was measured with detector D (530/30 nm band pass filter) for EGFP and detector C (585/42 nm band pass filter) for TdTomato fluorescent protein. To test the effect of different published trypsin treatments (Lundberg, 2003, Mol. Ther., 8:143 and Egorova et al., 2009, J. Gene Med.,11:772) in our internalization results, we used 0.5 mg/ml and 1 mg/ml of trypsin with or without 1 M NaCl for 1 or 15 min before cytometry analysis.

Competition Assay

To assess the binding specificity of T22-GFP-H6 to CXCR4, HeLa cells were grown in a 24-well plaque at 70% confluence in a competition assay. Cells were pre-incubated for 30 min with increasing amounts of the natural CXCR4 ligand SDF1alpha in Optipro, to reach 25 nM and 250 nM, or with the irrelevant proteins GFP-H6 and human alpha-galactosidase (both at 250 nM). Then, T22-GFP-H6 was added to the cultures at 25 nM and further incubated. One hour later, cells were treated with 1 mg/mL trypsin for 15 min and intracellular fluorescence determined by flow cytometry. Data were analyzed with WinMDI, Microsoft Excel 2003 and Sigmaplot 10 software.

Example 1

The Peptide T22 is Able to Promote the Internalization of Functional and Soluble Fused Proteins into Target CXCR4+ Cells.

Figure 3A:
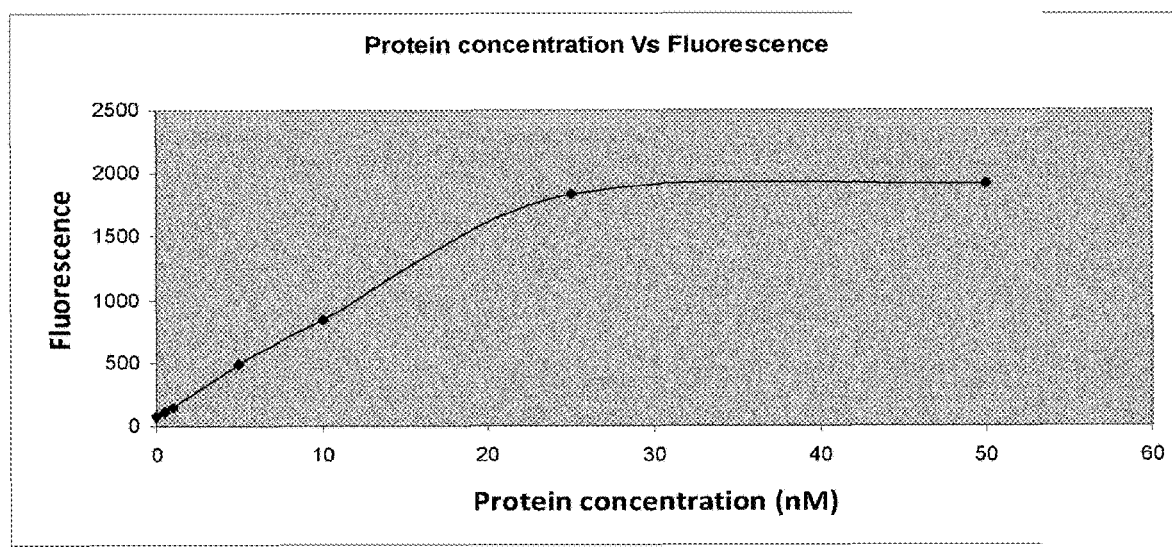
FIGS. 3A-3O. Characterization of T22-GFP-H6 entrance in HeLa cells.
Figure 3B:
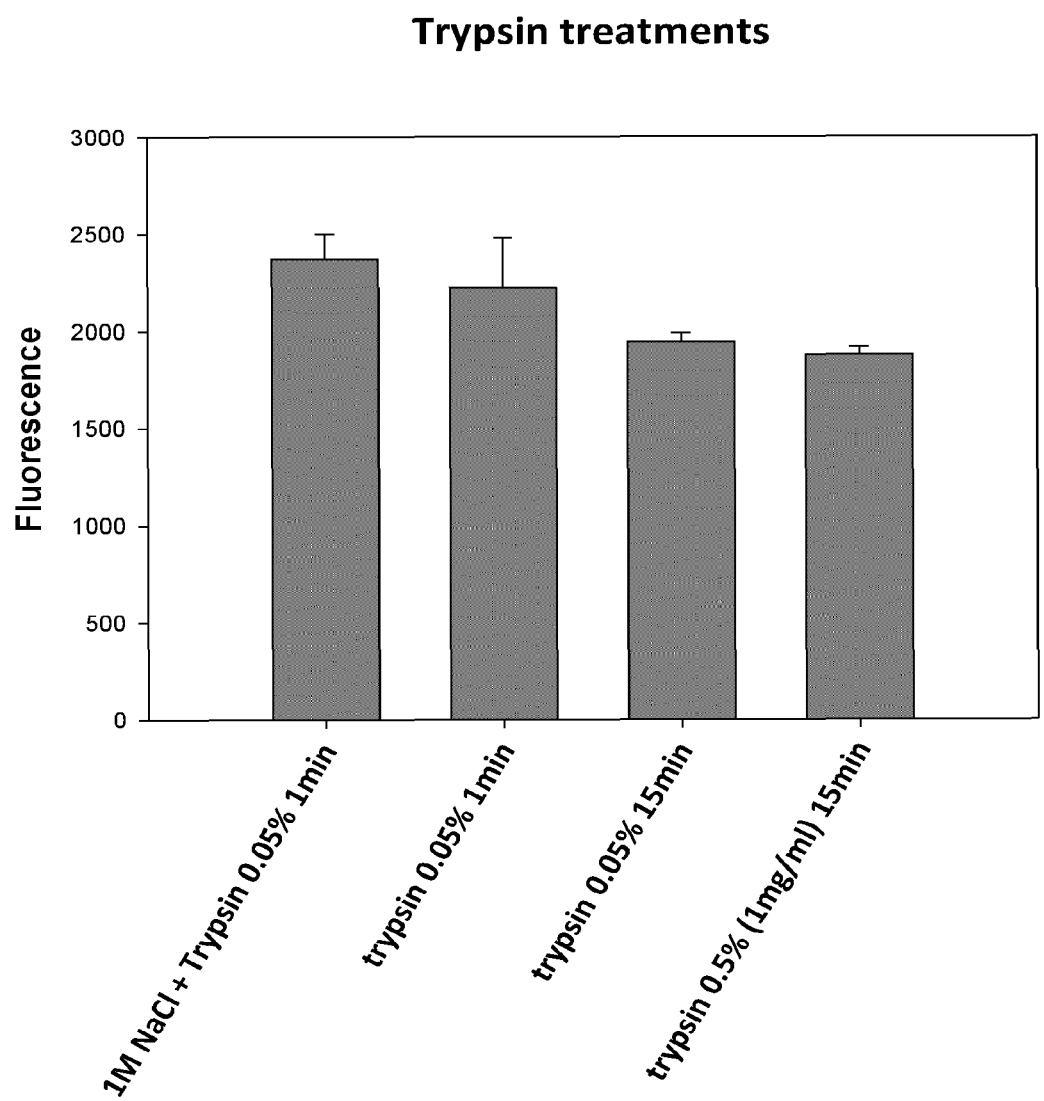
FIG. 3B Green fluorescent protein emission determined by flow cytometry of HeLa cells 20 h after exposure to 2 µM T22-GFP-H6, and with different trypsinization treatments previous to cytometry analysis.
Figure 3C:
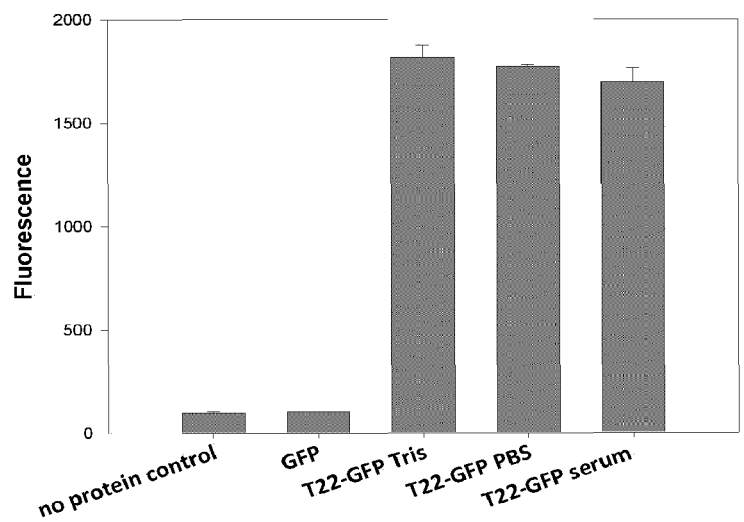
FIG. 3C Effect of serum on 2 µM T22-GFP-H6 internalization measured by flow cytometry and analyzed by confocal microscopy in the presence of complete medium (FIG. 3E) or Optipro (FIG. 3D), 20 h after protein addition.
Figure 3D:
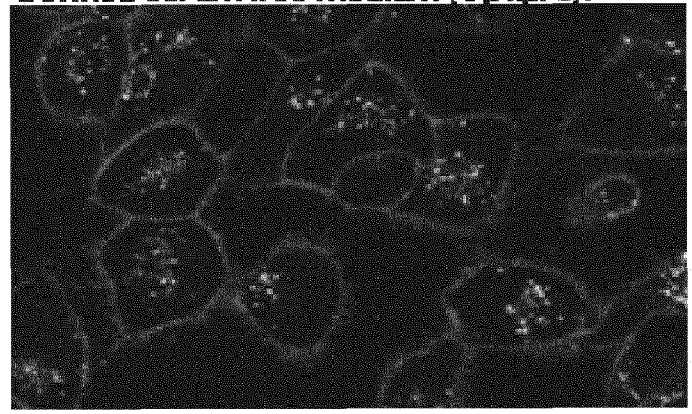
Figure 3E:
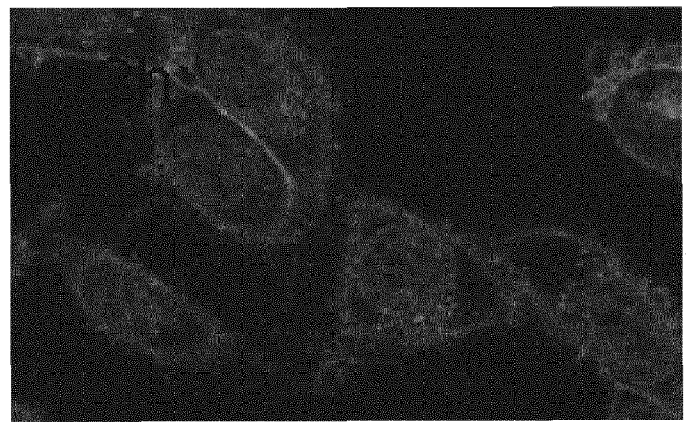

In this study, the internalization properties of four peptides, already described as CXCR4 ligands, namely T22, V1, vCCL2, CXCL12 (see Table 1) was investigated. This was done by constructing four model proteins in which these peptides had been fused to GFP-H6 (Table 2), rendering fully fluorescent proteins. When exposing cultured HeLa cells to these constructs, those in contact with T22-GFP-H6 were dramatically labelled with green fluorescence over the rest of peptides (FIGS. 1A, 1B and 2A, 2B, 2C, and 2D). This uptake was concentration dependent (see FIG. 3A) and observed even after treating the cells with trypsin after the binding of the fusion proteins to eliminate superficially attached protein (FIG. 3B). To assess that the signal was due to actual protein uptake, cultured cells were submitted to confocal analysis that confirmed the highly efficient internalization of T22-GFP-H6, and the poor penetrability of the rest of tested peptides (FIGS. 3C, 3D, 3E, 3F, 3G, 3H, 3I, 3J, 3K, 3L, 3M, 3N, and 3O).

Thus, the peptide T22 is able to promote the internalization of functional and soluble fused proteins into target CXCR4+ cells.

Example 2

The Peptide T22 is Able to Promote the Internalization and Expression of Plasmid DNA into Target CXCR4+ Cells.

Figure 3F:
FIG. 3F-3H are isosurface representation of HeLa cells within a 3D volumetric x-y-z data field after incubation with 2 µM T22-GFP-H6.
Figure 3G:
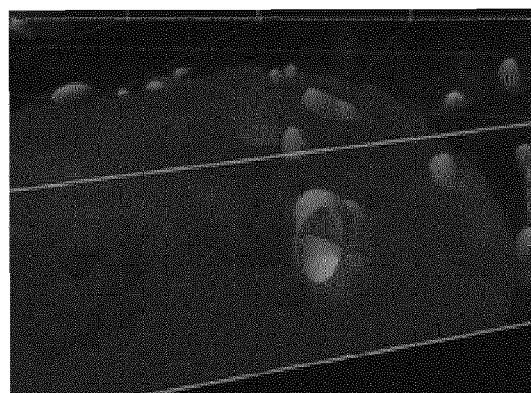
Figure 3H:
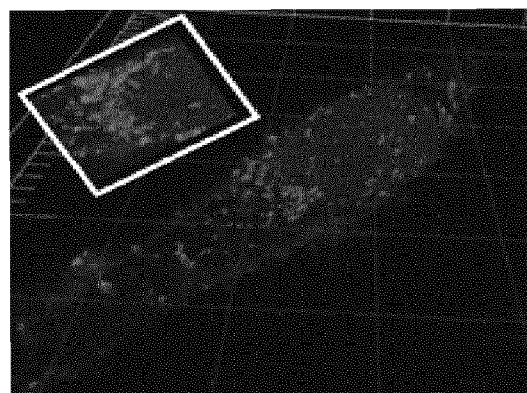
Figure 3I:
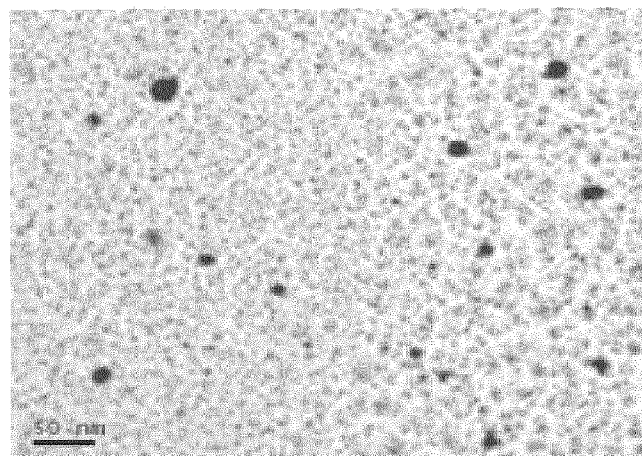
Figure 3J:
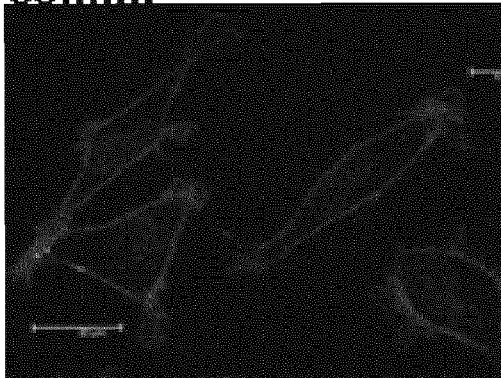
Figure 3K:
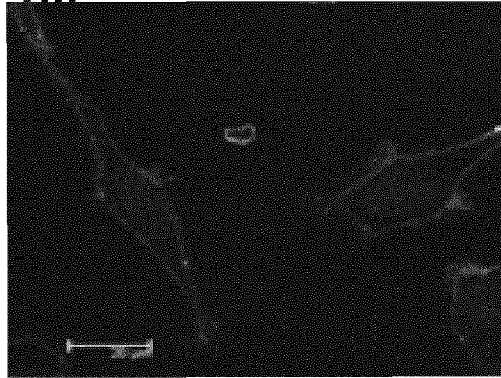
Figure 3L:
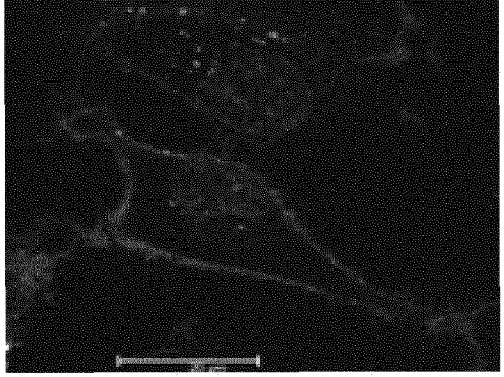
Figure 3M:
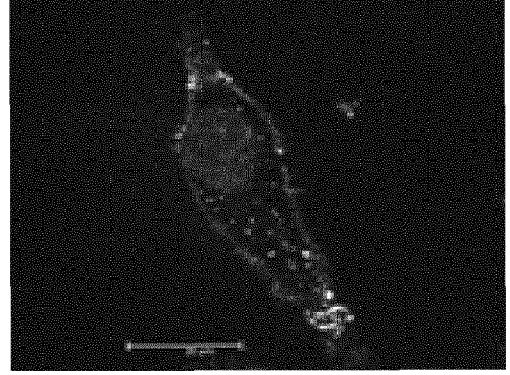
Figure 3N:
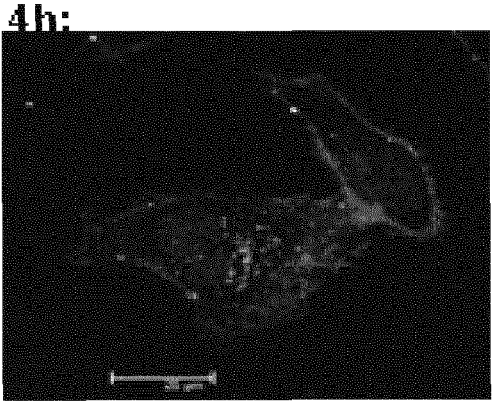
Figure 3O:
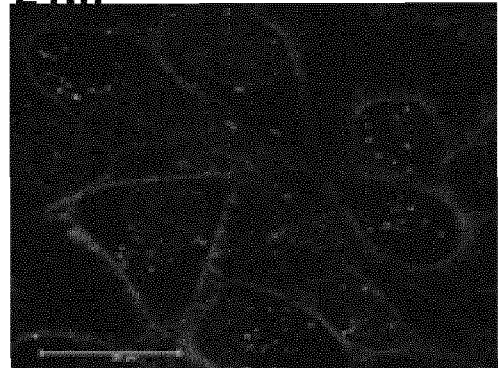
Figure 4A:
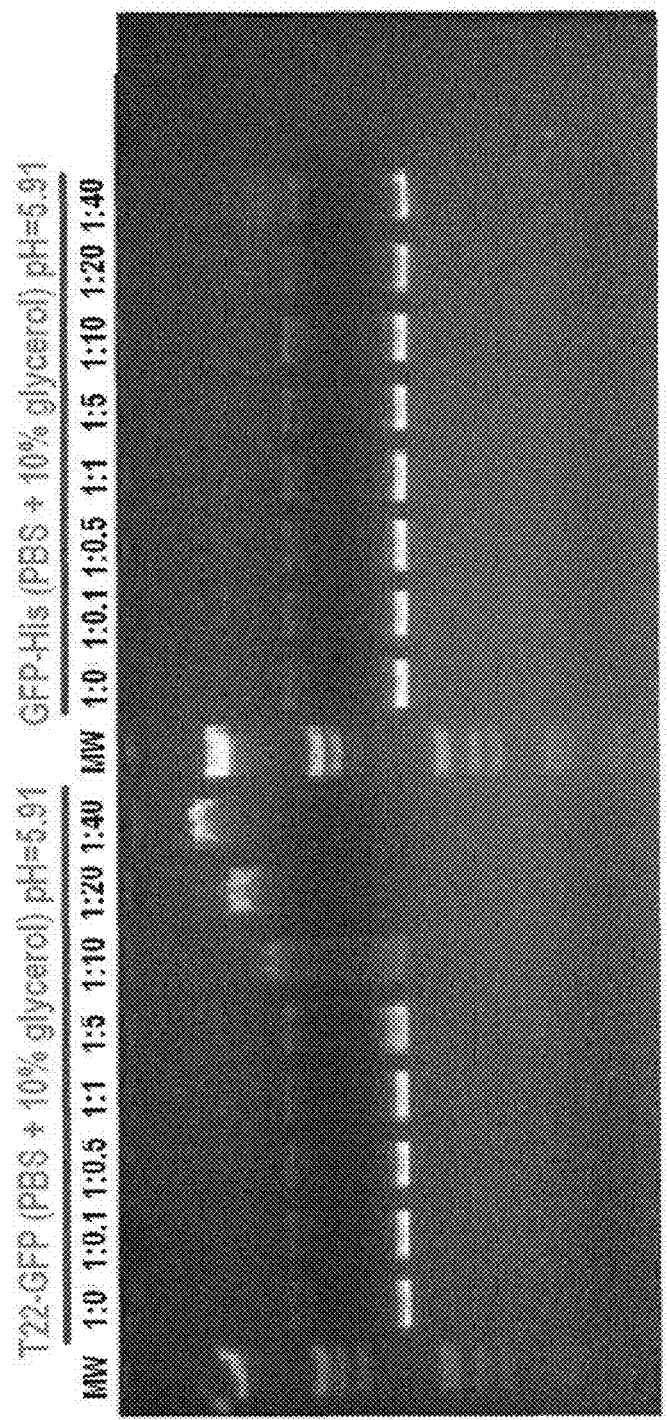

Different biological and physicochemical features of T22-GFP-H6 were determined by alternative procedures (FIGS. 3C, 3D, 3E, 3F, 3G, 3H, 3I, 3J, 3K, 3L, 3M, 3N, and 3O). Among them, it was noteworthy the perinuclear localization of T22-GFP-H6 and the presumed docking of the protein in the nuclear membrane (FIGS. 3F, 3G and 3H, see the inset). This suggested that apart from the potential of T22 in the delivery of functional proteins (in the model a fully fluorescent GFP shown in Example 1), this peptide could also deliver expressible DNA and eventually promote their entrance into the nuclear compartment. To explore this possibility, it was first determined whether T22-GFP-H6 could bind plasmid DNA in vitro, what was fully proved by DNA retardation assays (FIGS. 4A, 4B, 4C and 4D). Furthermore, the potential gene expression of the reporter TdTomato gene, encoding a red fluorescent protein, was analyzed when this gene was associated to T22-GFP-H6 complexes. The analysis of transfected HeLa cells (FIGS. 4B, 4C and 4D) indicated that the reporter gene is expressed, and not matching red (DNA expression) and green (T22-GFP-H6) fluorescence were clearly observed in those cultured cells.

Example 3

The Internalization of T22-GFP-H6 is Inhibited by a Natural Ligand of CXCR4

Figure 5:
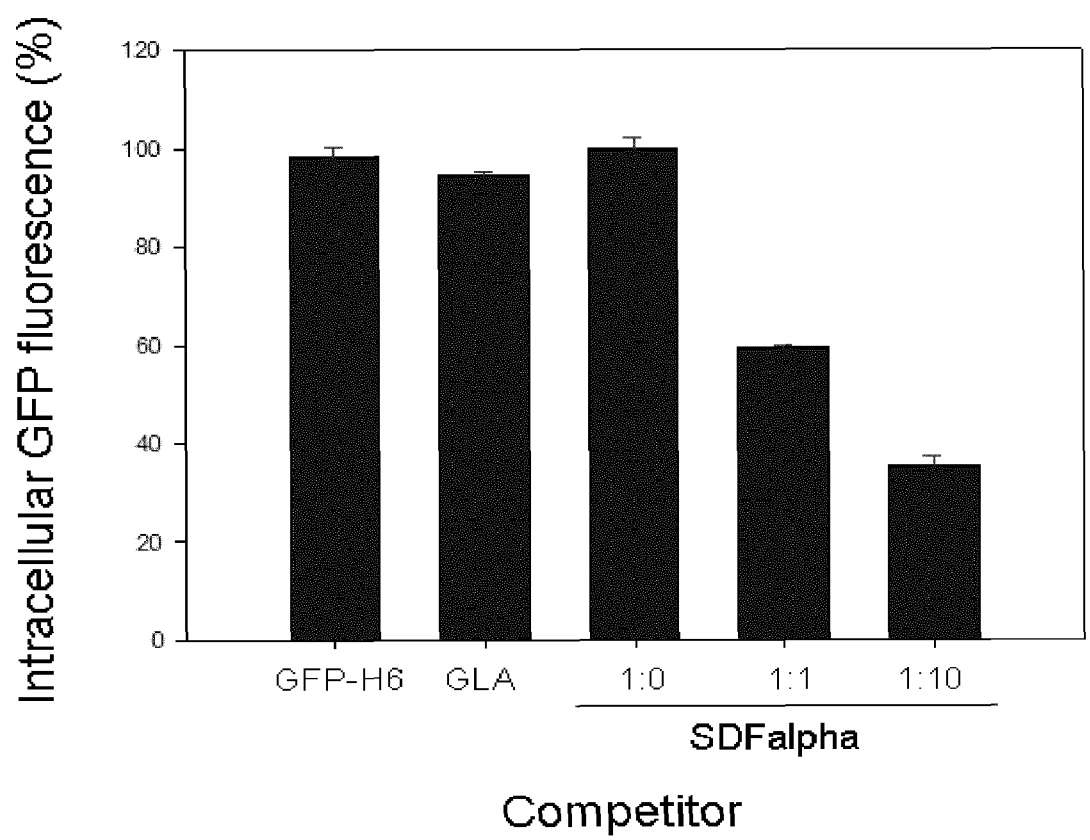
FIG. 5. Inhibition of T22-GFP-H6 internalization by a natural ligand of CXCR4, the protein SDFalpha, at different T22-GFP-H6/SDFalpha ratios (1:0, 1:1, 1:10). Two irrelevant proteins, GFP-H6 and GLA, were used as controls at a 1:10 ratio.
Figure 6:
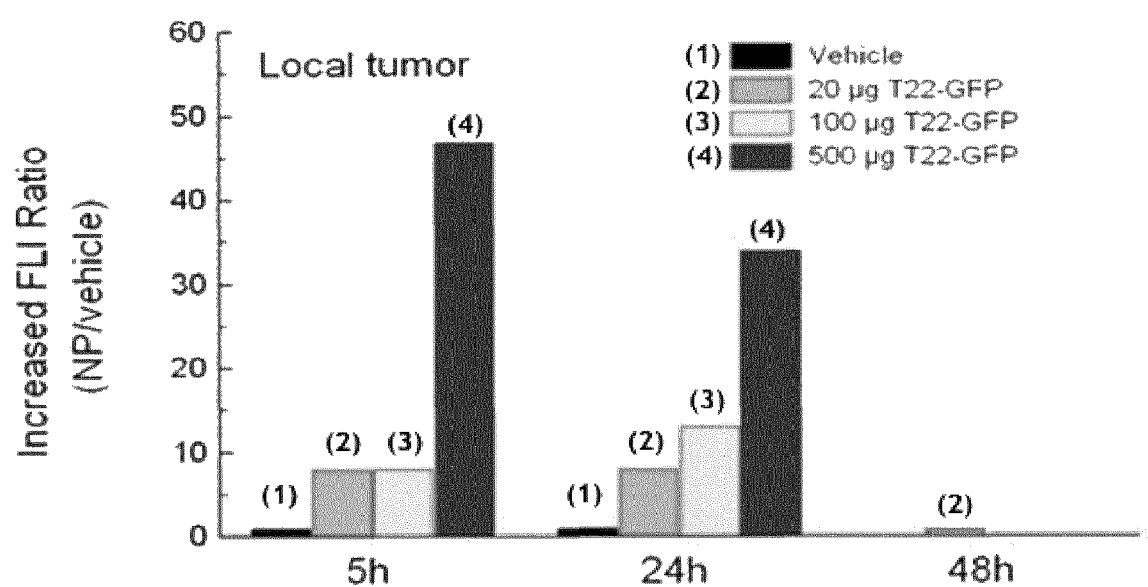
FIG. 6. Selective biodistribution of the T22-GFP, a fusion protein comprising T22 as a target moiety (which specifically binds to the CXCR4 receptor) and a green fluorescent protein, to primary tumor tissue derived from CXCR4+ SW1417 human colorectal cancer cells xenotransplanted in the cecum of immunosuppressed mice. Notice the 8-47 fold accumulation of T22-GFP, as measured by fluorescence quantitation, using a IVIS200 system (Xenogen) at a dose range varying form 20 to 500 ug, at several time points (5, 24 or 48 h), after intravenous single dose administration. No fluorescence is detected in primary tumor tissue in control mice treated with vehicle. Fluorescence in the stomach is due to ingested food, which does not differ between experimental and control animals. Black asterisk: Primary tumor.
Figure 7:
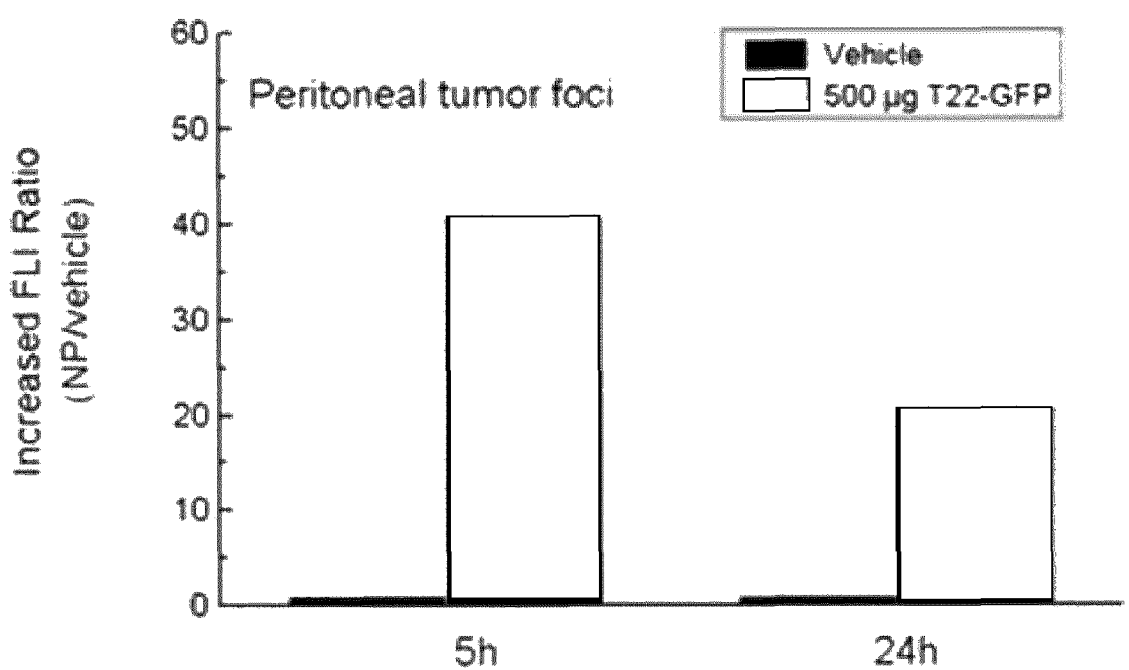
FIG. 7. Selective biodistribution of the T22-GFP to the peritoneal metastases and mesenteric and diaphragmatic lymph nodes derived from CXCR4+SW1417 human colorectal cancer cells xenotransplanted in the cecum of immunosuppressed mice. Notice the 20-40 fold accumulation of T22-GFP in peritoneal metastatic foci, as measured by fluorescence quantitation using a IVIS200 system (Xenogen) at a 500 ug dose at 5 h or 24 h after intravenous single dose administration. No fluorescence is detected in the liver parenchyma, pancreatic parenchyma, kidney, heart, non-tumor intestine, non-tumor lymph nodes, lung or spleen of the experimental or control (vehicle control) animal. Whereas accumulation of the T22-GFP fusion protein is observed in tumor tissues, no accumulation of T22-GFP is observed in normal tissues. Fluorescence is observed in the billiary vesicle (attached to the liver) or in the pancreas in both experimental and control animals, which could be attributed to fluorescent proteins secreted by these organs. Black asterisk: Primary tumor; Black arrow: Peritoneal metastasis.

The ability of a natural CXCR4 ligand (SDFalpha) to inhibit the internalization of T22-GFP-H6 was tested by contacting CXCR4+ cells with the T22-GFP-H6 in the presence of the protein SDFalpha, at different T22-GFP-H6/SDFalpha ratios (1:0, 1:1, 1:10). Two irrelevant proteins, GFP-H6 and GLA were used as controls at a 1:10 ratio. The results showed that SDFalpha was capable to inhibit in a dose-dependent manner the internalization of the T22-GFP-H6, whereas no effect was observed with the unrelated proteins (FIG. 5).

Example 4

Selective Biodistribution of the T22-GFP In Vivo to Primary Tumors

A fusion protein comprising T22 as a target moiety (which specifically binds to the CXCR4 receptor) and a green fluorescent protein was administered to immunosuppressed mice containing a primary tumor resulting from the xenotransplant of CXCR4+ SW1417 human colorectal cancer cells in the cecum of the mice. Distribution of T22-GFP was determined at several time points (5, 24 or 48 h) after intravenous single dose administration of a dose range varying form 20 to 500 ug. T22-GFP accumulated 8-47 fold with respect to control animals, as measured by fluorescence quantitation, using a IVIS200 system (Xenogen). No fluorescence is detected in primary tumor tissue in control mice treated with vehicle.

Example 5

Selective Biodistribution of the T22-GFP to the Peritoneal Metastases and Mesenteric and Diaphragmatic Lymph Nodes An intravenous single dose of 500 µg of T22-GFP was administered to mice showing peritoneal metastases and mesenteric and diaphragmatic lymph nodes derived from CXCR4+ SW1417 human colorectal cancer cells xenotransplanted in the cecum of immunosuppressed mice. T22-GFP accumulated 20-40 fold in peritoneal metastatic foci, as measured by fluorescence quantitation using a IVIS200 system (Xenogen) at 5 h or 24 h after. No fluorescence was detected in the liver parenchyma, pancreatic parenchyma, kidney, heart, non-tumor intestine, non-tumor lymph nodes, lung or spleen of the experimental or control (vehicle control) animal. Whereas accumulation of the T22-GFP fusion protein was observed in tumor tissues, no accumulation of T22-GFP was observed in normal tissues. Fluorescence was observed in the billiary vesicle (attached to the liver) or in the pancreas in both experimental and control animals, which could be attributed to fluorescent proteins secreted by these organs.

TABLE 1

Main physicochemical properties of the peptides used in this study.

| Peptide | Sequence | mer | Mw (Da) | P | N | Arg | pI | AI | H | SI |
|---|---|---|---|---|---|---|---|---|---|---|
| T22 | MRRWCYRKCYKGYCYRKCR (SEQ ID NO: 28) | 19 | 2623.1 | 8 | 0 | 5 | 9.96 | 0 | -1.516 | 39.06 (stable) |
| V1 | MLGASWHRPDKCCLGYQKRPLP (SEQ ID NO: 29) | 22 | 2557 | 4 | 1 | 2 | 9.38 | 57.73 | -0.705 | 55.14 (unstable) |
| vCCL2 | MLGASWHRPDKCCLGYQKRPLPQVLLSSWYPTSQLCSKPGVIFLTKRGRQVCADKSKDWVKKLMQQLPVTA (SEQ ID NO: 30) | 71 | 8103.6 | 12 | 3 | 4 | 9.9 | 79.58 | -0.361 | 37.48 (stable) |
| CXCL12 | MKPVSLSYRCPCRFFESHVARANVKHLKILNTPNCALQIVARLKNNNRQVCIDPKLKWIQEYLEKALN (SEQ ID NO: 31) | 68 | 7966.4 | 12 | 4 | 5 | 9.81 | 97.5 | -0.328 | 16.24 (stable) |

P: Positively charged amino acids; N: Negatively charged amino acids; Arg: Number of arginine residues; pI: Isoelectric point; AI: Aliphatic index; H: Hidrophobicity; SI: Stability index;

TABLE 2

Main physicochemical properties of the fusion proteins generated in this study.

| Fusion Protein | mer | Mw (Da) | S (%) | SF (FU/µg protein) | P | N | pI | AI | H | SI | TAS | HphoAS | HphiAS | NCP | NCT |
|---|---|---|---|---|---|---|---|---|---|---|---|---|---|---|---|
| T22-GFP-H6 (SEQ ID NO: 33) | 269 | 30691.5 | 100 | 13.76 (PBS) 22.8 (Tris) | 36 | 34 | 8.12 | 66.99 | -0.71 | 34.18 (stable) | 16039 | 8828 | 7212 | 3 | 0 |
| V1-GFP-H6 (SEQ ID NO: 34) | 272 | 30625.4 | 100 | 12.01 (PBS) 12.44 (Tris) | 32 | 35 | 6.62 | 70.92 | -0.653 | 35.85 (stable) | 14787 | 8405 | 6382 | -4 | -6 |
| vCCL2-GFP-H6 (SEQ ID NO: 35) | 321 | 36172 | 100 | 17.15 (PBS) 11.57 (Tris) | 40 | 37 | 8.38 | 73.74 | -0.585 | 34.89 (stable) | 24780 | 15428 | 9353 | 2 | 1 |
| CXCL12-GFP-H6 (SEQ ID NO: 36) | 318 | 36034.8 | 5.33 | 27.4 (PBS) 14.32 (Tris) | 40 | 38 | 8.11 | 77.52 | -0.58 | 29.85 (stable) | 17806 | 10007 | 7799 | 0 | 0 |

S: Solubility; SF: Specific fluorescence; P: Positively charged amino acids; N: Negatively charged amino acids; pI: Isoelectric point; AI: Aliphatic index; H: Hidrophobicity; SI: Stability index; TAS: Total accessibility to solvent; HphoAS: Hydrophobic accessibility to solvent; HphiAS: Hydrophilic accessibility to solvent; NCP: Net charge in PBS (pH = 7.4); NCT: Net charge in Tris (pH = 8)

The invention claimed is:

1. A conjugate comprising
   (i) a targeting peptide comprising the sequence RRWCYRKCYKGYCYRKCR (SEQ ID NO: 5) or a peptide with at least one conservative amino acid substitution in the sequence SEQ ID NO: 5, wherein the conservative amino acid substitution is selected from the following six groups each contain amino acids that are conservative substitutions for one another:
   1Alanine (A), Serine (S); Threonine (T);
   2Aspartic acid (D), Glutamic acid (E);
   3Asparagine (N), Glutamine (Q);
   4Arginine (R), Lysine (K);
   5Isoleucine (I), Leucine (L), Methionine (M), Valine (V); and
   6Phenylalanine (F), Tyrosine (Y), Tryptophan (W), and
   (ii) a therapeutic agent,
   wherein the targeting peptide specifically binds to chemokine receptor type 4 (CXCR4) and promotes internalization of the therapeutic agent in a cell expressing CXCR4 and wherein the therapeutic agent is a polypeptide or protein.

2. The conjugate according to claim 1 wherein the targeting peptide consists of the sequence RRWCYRKCYKGYCYRKCR (SEQ ID NO: 5).

3. The conjugate according to claim 1 wherein the therapeutic agent is a polypeptide.

4. The conjugate according to claim 3 wherein the therapeutic agent and the targeting peptide are part of a fusion protein.

5. The conjugate according in claim 1, wherein the therapeutic agent is provided within a nanotransporter and wherein the nanotransporter is coupled to the targeting peptide.

6. The conjugate according to claim 1, wherein the therapeutic agent is an antitumor agent.

7. The conjugate according to claim 6 wherein the antitumor agent is selected from the group consisting of
   (i) a cytotoxic polypeptide,
   (ii) an antiangiogenic polypeptide,
   (iii) a polypeptide encoded by a tumor suppressor gene,
   (iv) a pro-apoptotic polypeptide,
   (v) a polypeptide having anti-metastatic activity, and
   (vi) a polypeptide encoded by a polynucleotide which is capable of activating the immune response towards a tumor.

8. The conjugate according to claim 1, wherein the therapeutic agent is an antiretroviral agent.

9. The conjugate according to claim 1, wherein the therapeutic agent is selected from the group consisting of
   (i) an antiretroviral agent,
   (ii) a cytotoxic polypeptide, and
   (iii) a pro-apoptotic polypeptide.

10. A method for the treatment of cancer in a subject in need thereof wherein said cancer contains cells that express CXCR4 said method comprising the administration of a conjugate according to claim 7.

11. The method according to claim 10 wherein the cancer is pancreatic or colorectal cancer.

* * * * *

SEQUENCE LISTING

<160> NUMBER OF SEQ ID NOS: 37

<210> SEQ ID NO 1
<211> LENGTH: 14
<212> TYPE: PRT
<213> ORGANISM: Artificial Sequence
<220> FEATURE:
<223> OTHER INFORMATION: Peptide analog
<220> FEATURE:
<221> NAME/KEY: VARIANT
<222> LOCATION: (1)..(1)
<223> OTHER INFORMATION: /replace = "4-fluorobenzoyl-arginine"
<220> FEATURE:
<221> NAME/KEY: VARIANT
<222> LOCATION: (3)..(3)
<223> OTHER INFORMATION: /replace = "L-3-(2-naphthyl) alanine"
<220> FEATURE:
<221> NAME/KEY: VARIANT
<222> LOCATION: (8)..(8)
<223> OTHER INFORMATION: /replace = "L-citrulline"
<220> FEATURE:
<221> NAME/KEY: VARIANT
<222> LOCATION: (12)..(12)
<223> OTHER INFORMATION: /replace = "L-citrulline"

<400> SEQUENCE: 1

Xaa Arg Xaa Cys Tyr Glu Lys Xaa Pro Tyr Arg Xaa Cys Arg
1               5                   10

<210> SEQ ID NO 2
<211> LENGTH: 26
<212> TYPE: PRT
<213> ORGANISM: Artificial Sequence
<220> FEATURE:
<223> OTHER INFORMATION: Peptide biotinylated at the C-terminal residue

<400> SEQUENCE: 2

Lys Pro Val Ser Leu Ser Tyr Arg Ser Pro Ser Arg Phe Phe Glu Ser
1               5                   10                  15

His Lys Lys Lys Lys Lys Lys Lys Lys Lys
            20                  25

<210> SEQ ID NO 3
<211> LENGTH: 17
<212> TYPE: PRT
<213> ORGANISM: Artificial Sequence
<220> FEATURE:
<223> OTHER INFORMATION: Peptide biotinylated at the C-terminal residue

<400> SEQUENCE: 3

Lys Pro Val Ser Leu Ser Tyr Arg Lys Lys Lys Lys Lys Lys Lys Lys
1               5                   10                  15

Lys

<210> SEQ ID NO 4
<211> LENGTH: 19
<212> TYPE: PRT
<213> ORGANISM: Artificial Sequence
<220> FEATURE:
<223> OTHER INFORMATION: Peptide biotinylated at the C-terminal residue
<220> FEATURE:
<221> NAME/KEY: VARIANT
<222> LOCATION: (1)..(1)
<223> OTHER INFORMATION: /replace = "D-Leu"

<400> SEQUENCE: 4

Xaa Gly Ala Ser Trp His Arg Pro Asp Lys Lys Lys Lys Lys Lys
1               5                   10                  15

Lys Lys Lys

<210> SEQ ID NO 5
<211> LENGTH: 18
<212> TYPE: PRT
<213> ORGANISM: Artificial Sequence
<220> FEATURE:
<223> OTHER INFORMATION: Sequence comprised in the T22 peptide

<400> SEQUENCE: 5

Arg Arg Trp Cys Tyr Arg Lys Cys Tyr Lys Gly Tyr Cys Tyr Arg Lys
1               5                   10                  15

Cys Arg

<210> SEQ ID NO 6
<211> LENGTH: 14
<212> TYPE: PRT
<213> ORGANISM: Artificial Sequence
<220> FEATURE:
<223> OTHER INFORMATION: T140 peptide
<220> FEATURE:
<221> NAME/KEY: VARIANT
<222> LOCATION: (3)..(3)
<223> OTHER INFORMATION: /replace = "L-3-(2-naphtyl)alanine"
<220> FEATURE:
<221> NAME/KEY: VARIANT
<222> LOCATION: (8)..(8)
<223> OTHER INFORMATION: /replace = "D-Lys"
<220> FEATURE:
<221> NAME/KEY: VARIANT
<222> LOCATION: (12)..(12)
<223> OTHER INFORMATION: /replace = "L-citrulline"

<400> SEQUENCE: 6

Arg Arg Xaa Cys Tyr Arg Lys Xaa Pro Tyr Arg Xaa Cys Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: TN14003 peptide
<220> FEATURE:
<221> NAME/KEY: VARIANT
<222> LOCATION: (3)..(3)
<223> OTHER INFORMATION: /replace = "L-3-(2-naphtyl)alanine"
<220> FEATURE:
<221> NAME/KEY: VARIANT
<222> LOCATION: (6)..(6)
<223> OTHER INFORMATION: /replace = "Cit"
<220> FEATURE:
<221> NAME/KEY: VARIANT
<222> LOCATION: (8)..(8)
<223> OTHER INFORMATION: /replace = "D-Lys"
<220> FEATURE:
<221> NAME/KEY: VARIANT
<222> LOCATION: (12)..(12)
<223> OTHER INFORMATION: /replace = "L-citrulline"

<400> SEQUENCE: 7

Arg Arg Xaa Cys Tyr Xaa Lys Xaa Pro Tyr Arg Xaa Cys Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: TC14012 peptide
<220> FEATURE:

```
<221> NAME/KEY: VARIANT
<222> LOCATION: (3)..(3)
<223> OTHER INFORMATION: /replace = "L-3-(2-naphtyl)alanine"
<220> FEATURE:
<221> NAME/KEY: VARIANT
<222> LOCATION: (8)..(8)
<223> OTHER INFORMATION: /replace = "D-citrulline"
<220> FEATURE:
<221> NAME/KEY: VARIANT
<222> LOCATION: (12)..(12)
<223> OTHER INFORMATION: /replace = "L-citrulline"

<400> SEQUENCE: 8

Arg Arg Xaa Cys Tyr Glu Lys Xaa Pro Tyr Arg Xaa Cys Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: TE14011 peptide
<220> FEATURE:
<221> NAME/KEY: VARIANT
<222> LOCATION: (3)..(3)
<223> OTHER INFORMATION: /replace = "L-3-(2-naphtyl)alanine"
<220> FEATURE:
<221> NAME/KEY: VARIANT
<222> LOCATION: (6)..(6)
<223> OTHER INFORMATION: /replace = "L-citrulline"
<220> FEATURE:
<221> NAME/KEY: VARIANT
<222> LOCATION: (8)..(8)
<223> OTHER INFORMATION: /replace = "D-Glu"
<220> FEATURE:
<221> NAME/KEY: VARIANT
<222> LOCATION: (12)..(12)
<223> OTHER INFORMATION: /replace = "L-citrulline"

<400> SEQUENCE: 9

Arg Arg Xaa Cys Tyr Xaa Lys Xaa Pro Tyr Arg Xaa Cys Arg
1               5                   10

<210> SEQ ID NO 10
<211> LENGTH: 24
<212> TYPE: DNA
<213> ORGANISM: Artificial Sequence
<220> FEATURE:
<223> OTHER INFORMATION: Antisense oligonucleotide to CXCR4

<400> SEQUENCE: 10
ctgatcccct ccatggtaac cgct                                          24

<210> SEQ ID NO 11
<211> LENGTH: 24
<212> TYPE: DNA
<213> ORGANISM: Artificial Sequence
<220> FEATURE:
<223> OTHER INFORMATION: Antisense oligonucleotide to CXCR4

<400> SEQUENCE: 11
tatatactga tccccctccat ggta                                         24

<210> SEQ ID NO 12
<211> LENGTH: 23
<212> TYPE: DNA
<213> ORGANISM: Artificial Sequence
<220> FEATURE:
<223> OTHER INFORMATION: Antisense oligonucleotide to CXCR4

<400> SEQUENCE: 12
```
cctccatggt aaccgctggt tct                                              23

<210> SEQ ID NO 13
<211> LENGTH: 21
<212> TYPE: DNA
<213> ORGANISM: Artificial Sequence
<220> FEATURE:
<223> OTHER INFORMATION: CXCR4-specific siRNA
<220> FEATURE:
<221> NAME/KEY: modified_base
<222> LOCATION: (20)..(21)
<223> OTHER INFORMATION: /replace = "dT"

<400> SEQUENCE: 13
uaaaaucuuc cugcccacct t                                                21

<210> SEQ ID NO 14
<211> LENGTH: 21
<212> TYPE: DNA
<213> ORGANISM: Artificial Sequence
<220> FEATURE:
<223> OTHER INFORMATION: CXCR4-specific siRNA
<220> FEATURE:
<221> NAME/KEY: modified_base
<222> LOCATION: (20)..(21)
<223> OTHER INFORMATION: /replace = "dT"

<400> SEQUENCE: 14
ggaagcuguu ggcugaaaat t                                                21

<210> SEQ ID NO 15
<211> LENGTH: 64
<212> TYPE: DNA
<213> ORGANISM: Artificial Sequence
<220> FEATURE:
<223> OTHER INFORMATION: CXCR4-specific shRNA

<400> SEQUENCE: 15
gatccaggat ggtggtgttt caattccttc aagagaggaa ttgaaacacc accatccttt      60
ttgg                                                                   64

<210> SEQ ID NO 16
<211> LENGTH: 21
<212> TYPE: DNA
<213> ORGANISM: Artificial Sequence
<220> FEATURE:
<223> OTHER INFORMATION: cDNA sequence segment of CXCR4

<400> SEQUENCE: 16
aataaaatct tcctgcccac c                                                21

<210> SEQ ID NO 17
<211> LENGTH: 21
<212> TYPE: DNA
<213> ORGANISM: Artificial Sequence
<220> FEATURE:
<223> OTHER INFORMATION: cDNA sequence segment of CXCR4

<400> SEQUENCE: 17
aaggaagctg ttggctgaaa a                                                21

<210> SEQ ID NO 18
<211> LENGTH: 7
<212> TYPE: PRT
<213> ORGANISM: Artificial Sequence
<220> FEATURE:

```
<223> OTHER INFORMATION: peptide formed by residues 53-56 and residues
      57-59 of tetranectin

<400> SEQUENCE: 18

Gly Thr Lys Val His Met Lys
1               5

<210> SEQ ID NO 19
<211> LENGTH: 13
<212> TYPE: PRT
<213> ORGANISM: Artificial Sequence
<220> FEATURE:
<223> OTHER INFORMATION: Subsequence corresponding to amino acids number
      2037-2049 of fibronectin

<400> SEQUENCE: 19

Pro Gly Thr Ser Gly Gln Gln Pro Ser Val Gly Gln Gln
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Subsequence fragment corresponding to amino
      acids 2038-2042 of fibronectin

<400> SEQUENCE: 20

Gly Thr Ser Gly Gln
1               5

<210> SEQ ID NO 21
<211> LENGTH: 10
<212> TYPE: PRT
<213> ORGANISM: Artificial Sequence
<220> FEATURE:
<223> OTHER INFORMATION: Sequence of the upper hinge region of murine
      IgG3

<400> SEQUENCE: 21

Pro Lys Pro Ser Thr Pro Pro Gly Ser Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Linker peptide

<400> SEQUENCE: 22

Ala Pro Ala Glu Thr Lys Ala Glu Pro Met Thr
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Enterokinase cleavage site

<400> SEQUENCE: 23

Asp Asp Asp Asp Lys
1               5

<210> SEQ ID NO 24
<211> LENGTH: 5
```

```
<212> TYPE: PRT
<213> ORGANISM: Artificial Sequence
<220> FEATURE:
<223> OTHER INFORMATION: Factor Xa cleavage site

<400> SEQUENCE: 24

Ile Glu Asp Gly Arg
1               5

<210> SEQ ID NO 25
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 25

Leu Val Pro Arg Gly Ser
1               5

<210> SEQ ID NO 26
<211> LENGTH: 7
<212> TYPE: PRT
<213> ORGANISM: Artificial Sequence
<220> FEATURE:
<223> OTHER INFORMATION: TEV protease cleavage site

<400> SEQUENCE: 26

Glu Asn Leu Tyr Phe Gln Gly
1               5

<210> SEQ ID NO 27
<211> LENGTH: 8
<212> TYPE: PRT
<213> ORGANISM: Artificial Sequence
<220> FEATURE:
<223> OTHER INFORMATION: PreScission protease cleavage site

<400> SEQUENCE: 27

Leu Glu Val Leu Phe Gln Gly Pro
1               5

<210> SEQ ID NO 28
<211> LENGTH: 19
<212> TYPE: PRT
<213> ORGANISM: Artificial Sequence
<220> FEATURE:
<223> OTHER INFORMATION: T22 peptide

<400> SEQUENCE: 28

Met Arg Arg Trp Cys Tyr Arg Lys Cys Tyr Lys Gly Tyr Cys Tyr Arg
1               5                   10                  15

Lys Cys Arg

<210> SEQ ID NO 29
<211> LENGTH: 22
<212> TYPE: PRT
<213> ORGANISM: Artificial Sequence
<220> FEATURE:
<223> OTHER INFORMATION: V1 peptide

<400> SEQUENCE: 29

Met Leu Gly Ala Ser Trp His Arg Pro Asp Lys Cys Cys Leu Gly Tyr
1               5                   10                  15

Gln Lys Arg Pro Leu Pro
            20
```

<210> SEQ ID NO 30
<211> LENGTH: 71
<212> TYPE: PRT
<213> ORGANISM: Artificial Sequence
<220> FEATURE:
<223> OTHER INFORMATION: vCCL2 peptide

<400> SEQUENCE: 30

Met Leu Gly Ala Ser Trp His Arg Pro Asp Lys Cys Cys Leu Gly Tyr
1               5                   10                  15

Gln Lys Arg Pro Leu Pro Gln Val Leu Leu Ser Ser Trp Tyr Pro Thr
            20                  25                  30

Ser Gln Leu Cys Ser Lys Pro Gly Val Ile Phe Leu Thr Lys Arg Gly
        35                  40                  45

Arg Gln Val Cys Ala Asp Lys Ser Lys Asp Trp Val Lys Lys Leu Met
    50                  55                  60

Gln Gln Leu Pro Val Thr Ala
65                  70

<210> SEQ ID NO 31
<211> LENGTH: 68
<212> TYPE: PRT
<213> ORGANISM: Artificial Sequence
<220> FEATURE:
<223> OTHER INFORMATION: CXCL12 peptide

<400> SEQUENCE: 31

Met Lys Pro Val Ser Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn
65

<210> SEQ ID NO 32
<211> LENGTH: 8
<212> TYPE: PRT
<213> ORGANISM: Artificial
<220> FEATURE:
<223> OTHER INFORMATION: Linker region

<400> SEQUENCE: 32

Gly Gly Ser Ser Arg Ser Ser
1               5

<210> SEQ ID NO 33
<211> LENGTH: 269
<212> TYPE: PRT
<213> ORGANISM: Artificial
<220> FEATURE:
<223> OTHER INFORMATION: T22-GFP-H6

<400> SEQUENCE: 33

Met Arg Arg Trp Cys Tyr Arg Lys Cys Tyr Lys Gly Tyr Cys Tyr Arg
1               5                   10                  15

Lys Cys Arg Gly Gly Ser Ser Arg Ser Ser Ser Lys Gly Glu Glu Leu
            20                  25                  30

```
Phe Thr Gly Val Val Pro Ile Leu Val Glu Leu Asp Gly Asp Val Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Arg His Asp Phe Phe Lys Ser Ala
            100                 105                 110

Met Pro Glu Gly Tyr Val Gln Glu Arg Thr Ile Ser Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Met Val Leu Leu Glu Phe Val Thr Ala Ala Gly Ile Thr His
                245                 250                 255

Gly Met Asp Glu Leu Tyr Lys His His His His His His
            260                 265

<210> SEQ ID NO 34
<211> LENGTH: 271
<212> TYPE: PRT
<213> ORGANISM: Artificial
<220> FEATURE:
<223> OTHER INFORMATION: V1-GFP-H6

<400> SEQUENCE: 34

Leu Gly Ala Ser Trp His Arg Pro Asp Lys Cys Cys Leu Gly Tyr Gln
1               5                   10                  15

Lys Arg Pro Leu Pro Gly Gly Ser Ser Arg Ser Ser Ser Lys Gly Glu
            20                  25                  30

Glu Leu Phe Thr Gly Val Val Pro Ile Leu Val Glu Leu Asp Gly Asp
        35                  40                  45

Val Asn Gly His Lys Phe Ser Val Ser Gly Glu Gly Glu Gly Asp Ala
    50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Leu Thr Tyr Gly Val Gln
                85                  90                  95

Cys Phe Ser Arg Tyr Pro Asp His Met Lys Arg His Asp Phe Phe Lys
            100                 105                 110

Ser Ala Met Pro Glu Gly Tyr Val Gln Glu Arg Thr Ile Ser Phe Lys
        115                 120                 125
```

```
Asp Asp Gly Asn Tyr Lys Thr Arg Ala Glu Val Lys Phe Glu Gly Asp
            130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Asn Ser His Asn
                165                 170                 175

Val Tyr Ile Thr Ala Asp Lys Gln Lys Asn Gly Ile Lys Ala Asn Phe
            180                 185                 190

Lys Ile Arg His Asn Ile Glu Asp Gly Ser Val Gln Leu Ala Asp His
        195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr His Gly Met Asp Glu Leu Tyr Lys His His His His His His
            260                 265                 270

<210> SEQ ID NO 35
<211> LENGTH: 320
<212> TYPE: PRT
<213> ORGANISM: Artificial
<220> FEATURE:
<223> OTHER INFORMATION: vCCL2-GFP-H6

<400> SEQUENCE: 35

Leu Gly Ala Ser Trp His Arg Pro Asp Lys Cys Cys Leu Gly Tyr Gln
1               5                   10                  15

Lys Arg Pro Leu Pro Gln Val Leu Leu Ser Ser Trp Tyr Pro Thr Ser
            20                  25                  30

Gln Leu Cys Ser Lys Pro Gly Val Ile Phe Leu Thr Lys Arg Gly Arg
        35                  40                  45

Gln Val Cys Ala Asp Lys Ser Lys Asp Trp Val Lys Lys Leu Met Gln
50                  55                  60

Gln Leu Pro Val Thr Ala Gly Gly Ser Ser Arg Ser Ser Ser Lys Gly
65                  70                  75                  80

Glu Glu Leu Phe Thr Gly Val Val Pro Ile Leu Val Glu Leu Asp Gly
                85                  90                  95

Asp Val Asn Gly His Lys Phe Ser Val Ser Gly Glu Gly Glu Gly Asp
            100                 105                 110

Ala Thr Tyr Gly Lys Leu Thr Leu Lys Phe Ile Cys Thr Thr Gly Lys
        115                 120                 125

Leu Pro Val Pro Trp Pro Thr Leu Val Thr Thr Leu Thr Tyr Gly Val
    130                 135                 140

Gln Cys Phe Ser Arg Tyr Pro Asp His Met Lys Arg His Asp Phe Phe
145                 150                 155                 160

Lys Ser Ala Met Pro Glu Gly Tyr Val Gln Glu Arg Thr Ile Ser Phe
                165                 170                 175

Lys Asp Asp Gly Asn Tyr Lys Thr Arg Ala Glu Val Lys Phe Glu Gly
            180                 185                 190

Asp Thr Leu Val Asn Arg Ile Glu Leu Lys Gly Ile Asp Phe Lys Glu
        195                 200                 205

Asp Gly Asn Ile Leu Gly His Lys Leu Glu Tyr Asn Tyr Asn Ser His
    210                 215                 220
```

Asn Val Tyr Ile Thr Ala Asp Lys Gln Lys Asn Gly Ile Lys Ala Asn
225                 230                 235                 240

Phe Lys Ile Arg His Asn Ile Glu Asp Gly Ser Val Gln Leu Ala Asp
            245                 250                 255

His Tyr Gln Gln Asn Thr Pro Ile Gly Asp Gly Pro Val Leu Leu Pro
        260                 265                 270

Asp Asn His Tyr Leu Ser Thr Gln Ser Ala Leu Ser Lys Asp Pro Asn
    275                 280                 285

Glu Lys Arg Asp His Met Val Leu Leu Glu Phe Val Thr Ala Ala Gly
290                 295                 300

Ile Thr His Gly Met Asp Glu Leu Tyr Lys His His His His His His
305                 310                 315                 320

<210> SEQ ID NO 36
<211> LENGTH: 318
<212> TYPE: PRT
<213> ORGANISM: Artificial
<220> FEATURE:
<223> OTHER INFORMATION: CXCL12-GFP-H6

<400> SEQUENCE: 36

Met Lys Pro Val Ser Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Gly Gly Ser Arg Ser Ser Lys Gly Glu Glu
65                  70                  75                  80

Leu Phe Thr Gly Val Val Pro Ile Leu Val Glu Leu Asp Gly Asp Val
                85                  90                  95

Asn Gly His Lys Phe Ser Val Ser Gly Glu Gly Glu Gly Asp Ala Thr
            100                 105                 110

Tyr Gly Lys Leu Thr Leu Lys Phe Ile Cys Thr Thr Gly Lys Leu Pro
        115                 120                 125

Val Pro Trp Pro Thr Leu Val Thr Thr Leu Thr Tyr Gly Val Gln Cys
    130                 135                 140

Phe Ser Arg Tyr Pro Asp His Met Lys Arg His Asp Phe Phe Lys Ser
145                 150                 155                 160

Ala Met Pro Glu Gly Tyr Val Gln Glu Arg Thr Ile Ser Phe Lys Asp
                165                 170                 175

Asp Gly Asn Tyr Lys Thr Arg Ala Glu Val Lys Phe Glu Gly Asp Thr
            180                 185                 190

Leu Val Asn Arg Ile Glu Leu Lys Gly Ile Asp Phe Lys Glu Asp Gly
        195                 200                 205

Asn Ile Leu Gly His Lys Leu Glu Tyr Asn Tyr Asn Ser His Asn Val
    210                 215                 220

Tyr Ile Thr Ala Asp Lys Gln Lys Asn Gly Ile Lys Ala Asn Phe Lys
225                 230                 235                 240

Ile Arg His Asn Ile Glu Asp Gly Ser Val Gln Leu Ala Asp His Tyr
                245                 250                 255

Gln Gln Asn Thr Pro Ile Gly Asp Gly Pro Val Leu Leu Pro Asp Asn
            260                 265                 270

```
His Tyr Leu Ser Thr Gln Ser Ala Leu Ser Lys Asp Pro Asn Glu Lys
        275                 280                 285

Arg Asp His Met Val Leu Leu Glu Phe Val Thr Ala Ala Gly Ile Thr
    290                 295                 300

His Gly Met Asp Glu Leu Tyr Lys His His His His His His
305                 310                 315

<210> SEQ ID NO 37
<211> LENGTH: 14
<212> TYPE: PRT
<213> ORGANISM: Artificial
<220> FEATURE:
<223> OTHER INFORMATION: TZ14011 peptide
<220> FEATURE:
<221> NAME/KEY: VARIANT
<222> LOCATION: (8)..(8)
<223> OTHER INFORMATION: /replace="D-Lysine"

<400> SEQUENCE: 37

Arg Arg Tyr Cys Tyr Arg Lys Xaa Pro Tyr Arg Lys Cys Arg
1               5                   10
```